United States Patent
Sodickson et al.

(10) Patent No.: US 9,903,921 B2
(45) Date of Patent: Feb. 27, 2018

(54) APPARATUS, METHOD AND COMPUTER-ACCESSIBLE MEDIUM FOR NONINVASIVE DETERMINATION OF ELECTRICAL PROPERTIES OF TISSUES AND MATERIALS

(75) Inventors: Daniel K. Sodickson, Larchmont, NY (US); Yudong Zhu, Scarsdale, NY (US)

(73) Assignee: New York University, New York, NY (US)

( * ) Notice: Subject to any disclaimer, the term of this patent is extended or adjusted under 35 U.S.C. 154(b) by 1785 days.

(21) Appl. No.: 13/314,105

(22) Filed: Dec. 7, 2011

(65) Prior Publication Data

US 2012/0150458 A1 Jun. 14, 2012

Related U.S. Application Data

(60) Provisional application No. 61/420,694, filed on Dec. 7, 2010.

(51) Int. Cl.
| | |
|---|---|
| *G01R 15/00* | (2006.01) |
| *G01R 33/12* | (2006.01) |
| *G01R 33/48* | (2006.01) |
| *G01R 33/3415* | (2006.01) |
| *G01R 33/28* | (2006.01) |

(Continued)

(52) U.S. Cl.
CPC ........ *G01R 33/1215* (2013.01); *A61B 5/0035* (2013.01); *A61B 5/055* (2013.01);
(Continued)

(58) Field of Classification Search
CPC ..... A61B 5/0536; A61B 5/055; A61B 5/0035; A61B 5/0037; G01R 33/4808;
(Continued)

(56) References Cited

U.S. PATENT DOCUMENTS

| | | | |
|---|---|---|---|
| 6,448,788 B1 * | 9/2002 | Meaney | A61B 5/0507 324/637 |
| 7,795,870 B2 | 9/2010 | Sodickson et al. | |

(Continued)

OTHER PUBLICATIONS

International Search Report for International Application No. PCT/US2011/063844 dated Jul. 2, 2012.
(Continued)

*Primary Examiner* — An Do
(74) *Attorney, Agent, or Firm* — Andrews Kurth Kenyon LLP

(57) ABSTRACT

Apparatus, method, and computer-accessible medium embodiments for a noninvasive mapping of electrical properties of tissues or materials. For example, it is possible to apply a plurality of stimulations to a target. It is possible to receive at least one signal from the target in response to the applied stimulations. Further, it is possible to process the at least one signal to determine electromagnetic-field-related quantities associated with the stimulations and the target response. Also, it is possible to supply the electromagnetic-field-related quantities to a system of equations relating these quantities to a plurality of electrical property values and residual field-related unknown values of the at least one target. It is also possible to determine a solution to the system of equations, including determining at least one electrical property of the at least one target.

65 Claims, 5 Drawing Sheets

(51) Int. Cl.
*G01R 33/58* (2006.01)
*A61B 5/053* (2006.01)
*A61B 5/055* (2006.01)
*A61B 5/00* (2006.01)

(52) U.S. Cl.
CPC .......... *A61B 5/0536* (2013.01); *G01R 33/288* (2013.01); *G01R 33/3415* (2013.01); *G01R 33/4808* (2013.01); *G01R 33/583* (2013.01)

(58) Field of Classification Search
CPC .............. G01R 33/3415; G01R 33/288; G01R 33/583; G01R 33/3607; G01R 33/5612
USPC .................................... 702/57; 324/200, 629
See application file for complete search history.

(56) References Cited

U.S. PATENT DOCUMENTS

| 2006/0125475 | A1 | 6/2006 | Sodickson et al. |
| 2009/0093709 | A1 | 4/2009 | Patel et al. |
| 2012/0146637 | A1* | 6/2012 | Zhu ........................ G01R 33/48 324/307 |

OTHER PUBLICATIONS

Ohlinger et al. "Ultimate intrinsic signal to noise ratio for parallel mri electromagnetic field considerations," Magnetic Resonance in Medicine, vol. 50, Issue5, pp. 101 (2003).

* cited by examiner

APPARATUS, METHOD AND COMPUTER-ACCESSIBLE MEDIUM FOR NONINVASIVE DETERMINATION OF ELECTRICAL PROPERTIES OF TISSUES AND MATERIALS

CROSS-REFERENCE TO RELATED APPLICATION(S)

This application claims priority to U.S. Provisional Application Ser. No. 61/420,694, filed on Dec. 7, 2010, the disclosure of which is incorporated by reference herein in its entirety.

FIELD OF THE DISCLOSURE

The present disclosure relates to mapping electrical properties of tissues or materials, and more specifically to apparatus, method, and computer-accessible medium for a noninvasive mapping of electrical properties of tissues or materials.

BACKGROUND INFORMATION

A prospect of noninvasive mapping of the electrical properties of tissues and materials has long been contemplated by scientists. "Electrical prospection" techniques have a long and rich history, in which a panoply of probes and innovative algorithms have been brought to bear in an attempt to solve the inherently ill-conditioned inverse problem associated with deducing internal electrical property maps from nondestructive external measurements. Despite the intrinsic difficulty of the problem and the absence of widespread successes with broad utilization so far, strong interest has persisted to the present day. This is likely because robust determination of the spatial distribution of electrical conductivity and permittivity would enable a wide range of applications in a similarly wide range of fields, from materials science to clinical diagnostics.

In the area of materials science, noninvasive mapping of the electrical properties of materials would expand the capabilities of nondestructive testing, with potential applications in manufacturing, geology, archaeology, forensics, etc. Meanwhile, in the biomedical arena, the visualization of localized changes in conductivity and permittivity could provide biophysical information complementary to that available from currently available imaging modalities such as Magnetic Resonance Imaging (MRI), Computed Tomography (CT), or ultrasound. Magnetoencephalography or electrocardiography can track intrinsic electrical activity in the brain or the heart, albeit at coarse spatial resolution; however, these modalities do not provide direct information about the electrical substrate of otherwise passive tissues. Indeed, all tissues are electromagnetic entities, with varying abilities to carry currents and store charges. Current-carrying and charge-storage capacities represent fundamental properties of the tissue microenvironment which might be expected to provide valuable information about disease processes, e.g. involving membrane derangements, muscle dysfunction, fluid accumulation, etc. It is known from invasive measurements that the electrical properties of tumors can differ dramatically from those of healthy tissue, making cancer a prominent target for early testing of techniques such as Electrical Impedance Tomography (EIT). Moreover, knowledge of the spatial distribution of electrical conductivity and permittivity would be valuable as a practical adjunct for various existing diagnostic and therapeutic technologies. The ability of heterogeneous tissues to respond to externally applied electromagnetic fields can dictate the success of therapeutic interventions such as transcranial magnetic stimulation or radiofrequency ablation. Interactions of electromagnetic fields with the body can distort images obtained with high-field MRI scanners, limiting the practical use of these powerful devices. Knowledge of electrical properties could be used to correct these distortions.

Previous approaches to electrical property mapping, also commonly referred to as electrical impedance imaging, may be classified according to two complementary criteria: a) use of injected currents versus applied fields, and b) reliance upon surface measurements versus interior data. EIT represents the canonical surface-based technique using injected currents. Alternative surface-based techniques which avoid direct application of currents include Microwave Tomography (MWT) and Magnetic Induction Tomography (MIT), as well as less well-known techniques such as noise tomography and Radiofrequency Impedance Mapping (RFIM). All such electrical prospection techniques utilize the solution of ill-posed inverse problems, which carry with them fundamental challenges of robustness, spatial resolution, etc. Once it was recognized that MRI may be used as a probe of the internal distribution of currents and magnetic fields, however, new techniques for impedance mapping began to emerge, including the injected-current-based MREIT approach, and the field-based electrical properties tomography (EPT) technique. These techniques circumvent the fundamental limitations of surface-based inverse problems, but they must contend with the fact that MRI generally provides only partial information about interior currents and fields.

The EPT technique, for example, achieves noninvasive electrical property mapping without injected currents by manipulating maps of RF transmitter sensitivity and MR signal phase. Results with EPT to date have been promising, with early in vivo studies in patient populations just emerging. However, EPT suffers from a fundamental lack of access to absolute RF phase, as all measurable phases are expressed in relation to some unknown reference phase distribution. This limitation has for many years been considered inescapable—a basic feature of the elementary processes by which we detect magnetic resonance signals. EPT circumvents this limitation to some extent by using a carefully-chosen coil design (a birdcage) and associated symmetry assumptions dictating field behavior in the body. However, these assumptions generally fail preferentially at high field strength—precisely where field curvature is greatest and electrical property maps would otherwise be expected to be most effective, not to mention most valuable for understanding tissue-field interactions that affect MR image quality and safety. It is also not known a priori precisely where and how the EPT approximation will break down for any particular body, opening up the possibility of unrecognized errors in property estimation.

Thus, there remains a need to provide apparatus, methods and computer-accessible mediums for noninvasive determination of electrical properties of tissues and materials.

SUMMARY OF EXEMPLARY EMBODIMENTS

According to certain exemplary embodiments of the present disclosure, exemplary architectures, apparatus, methods, and computer-accessible medium for determining at least one electrical property of at least one target. The exemplary embodiments can include an exemplary method. The exemplary method can include applying a plurality of stimulations to the at least one target. The exemplary method can include receiving at least one signal from the at least one target in response to the applied stimulations. The exemplary method can include processing the at least one signal to determine electromagnetic-field-related quantities associated with the stimulations and the target response. The exemplary method can include supplying the electromagnetic-field-related quantities to a system of equations relating these quantities to a plurality of electrical property values and residual field-related unknown values of the at least one target. The exemplary method can include determining a solution to the system of equations, including determining at least one electrical property of the at least one target.

In certain exemplary embodiments, the at least one target can include at least one of a tissue or a material. In certain exemplary embodiments, the at least one electrical property can include at least one of a conductivity, a permittivity, or a permeability of the at least one target. In certain exemplary embodiments, at least one of the conductivity, permittivity, or the permeability can be at least one of a scalar or a tensor. Certain exemplary embodiments can also include mapping the at least one electrical property of the at least one target.

In certain exemplary embodiments, the stimulations can include at least one of an injection of a current or generation of an electromagnetic field. In certain exemplary embodiments, the signal can include information representative of at least one of a current or an electromagnetic field. In certain exemplary embodiments, the stimulations can be created by a plurality of radiofrequency transmitter coils. In certain exemplary embodiments, the signal can be detected in at least one radiofrequency receiver coil. In certain exemplary embodiments, the signal can be a magnetic resonance signal. In certain exemplary embodiments, the residual field-related unknown values can include at least one of an electromagnetic field phase or a magnetization value. In certain exemplary embodiments, electromagnetic-field-related quantities can include a transmit and/or a receive sensitivity distribution. In certain exemplary embodiments, complementary information from transmit and receive sensitivity distributions can be used to resolve ambiguities in electrical property values and residual field-related unknown values.

The exemplary embodiments can also include determining local expressions for Maxwell equations relating field curvature to electrical properties of interest, including the at least one electrical property of the at least one target. The exemplary embodiments can also include determining composite expressions by expressing the true laboratory-frame magnetic fields as combinations of measurable quantities and residual unknowns, wherein the measurable quantities include at least one of: directly measurable quantities or quantities derived from the directly measurable quantities. The exemplary embodiments can also include inserting these composite expressions into the local Maxwell equations, and separating terms associated with measurable quantities from those associated with the residual unknowns and local values of the at least one electrical property. Further, the exemplary embodiments can also include grouping the terms to form equations in which known coefficients represent local derivatives of the measurable quantities, and the unknowns include local derivatives of distributions of the residual unknowns, as well as local values of the at least one electrical property.

In certain exemplary embodiments, separating terms include using a product law of differentiation. In certain exemplary embodiments, determining a solution can include solving for electrical conductivity and permittivity separately in two steps. In certain exemplary embodiments, determining a solution can comprise finding and applying one or more linear matrix inverses. In certain exemplary embodiments, determining a solution can comprise applying a nonlinear optimization algorithm. In certain exemplary embodiments, determining a solution can include use of a noise and/or error covariance matrix to control noise/error propagation. In certain exemplary embodiments, the noise/error covariance matrix can include diagonal terms associated with amplitude of field-related quantities.

In certain exemplary embodiments, the plurality of stimulations and the at least one signal can be selected so as to maintain good conditioning of the system of equations. In certain exemplary embodiments, the selection of stimulations and signal can be aimed at ensuring sufficient transmit and/or receive field variation in all directions for robust solution of the system of equations. In certain exemplary embodiments, determining a solution can include use of Tikhonov regularization. In certain exemplary embodiments, a transmit-receive array containing at least three elements can be used. In certain exemplary embodiments, more than three coil pairs are used to improve conditioning. In certain exemplary embodiments, the system of equations can be derived by forming local combinations of electromagnetic-field-related quantities which reduce the contributions of some residual unknowns as compared with using uncombined quantities.

In certain exemplary embodiments, determining a solution can include use of at least one Savitsky Golay derivative. In certain exemplary embodiments, the system of equations can be derived by forming local combinations of electromagnetic-field-related quantities which improve the robustness of solution as compared with using uncombined quantities. In certain exemplary embodiments, the combinations can be derived from a matched filter or rephased combination. In certain exemplary embodiments, the combinations can be selected to generate slow local variation in the electromagnetic-field-related quantities. In certain exemplary embodiments, the local combinations can be performed on transmit-field-related quantities. In certain exemplary embodiments, the local combinations can be performed on receive-field-related quantities. In certain exemplary embodiments, the local combinations can be selected to produce a tailored phase reference combination at each point of interest.

The exemplary embodiment can also include deriving a plurality of estimations of at least one unknown value for the at least one target based on the measured characteristics. The exemplary embodiment can also include determining a consensus of the estimations. The exemplary embodiment can also include determining the at least one property of the at least one target using the consensus. The exemplary embodiment can also include constructing at least one of transmit sensitivity distributions, receive sensitivity distributions, or at least one combination thereof, each having at least one unknown value for the at least one tissue. The exemplary embodiment can also include determining a consensus of the at least one transmit sensitivity distributions, receive sensitivity distributions, or combinations thereof. Also, the exemplary embodiment can include determining the at least one property of the at least one tissue based on the consensus.

Additional exemplary embodiments can include a non-transitory computer readable medium including instructions thereon that are accessible by a hardware processing arrangement, wherein, when the processing arrangement executes the instructions, the processing arrangement can be configured to apply a plurality of stimulations to at least one target, receive at least one signal from the at least one target in response to the applied stimulations, process the at least one signal to determine electromagnetic-field-related quantities associated with the stimulations and the target response, supply the electromagnetic-field-related quantities to a system of equations relating these quantities to a plurality of electrical property values and residual field-related unknown values of the at least one target and determine a solution to the system of equations, including determining at least one electrical property of the at least one target.

Another exemplary embodiment can include an apparatus for determining at least one property of at least one target. The exemplary apparatus can include a plurality of transmitters which is configured to apply a plurality of stimulations to the at least one target, a plurality of receivers which is configured to receive at least one signal from the at least one target in response to the applied stimulations, and a non-transitory computer readable medium. The exemplary computer readable medium can including instructions thereon that are accessible by a hardware processing arrangement, wherein, when the processing arrangement executes the instructions, the processing arrangement is configured to process the at least one signal to determine electromagnetic-field-related quantities associated with the stimulations and the target response, supply the electromagnetic-field-related quantities to a system of equations relating these quantities to a plurality of electrical property values and residual field-related unknown values of the at least one target, and determine a solution to the system of equations, including determining at least one electrical property of the at least one target.

Another exemplary embodiment can include a method for determining a magnetization distribution of at least one target. The exemplary method can apply a plurality of stimulations to the at least one target, receive at least one signal from the at least one target in response to the applied stimulations, process the at least one signal to determine electromagnetic-field-related quantities associated with the stimulations and the target response, supply the electromagnetic-field-related quantities to a system of equations relating these quantities to a plurality of magnetization values and residual field-related unknown values of the at least one target, and determine a solution to the system of equations, including determining at least one magnetization distribution of the at least one target.

Another exemplary embodiment can include a method for determining a field-related phase distribution of at least one target. The exemplary method can apply a plurality of stimulations to the at least one target, receive at least one signal from the at least one target in response to the applied stimulations, process the at least one signal to determine electromagnetic-field-related quantities associated with the stimulations and the target response, supply the electromagnetic-field-related quantities to a system of equations relating these quantities to a plurality of field-related phase values and residual field-related unknown values of the at least one target, and determine a solution to the system of equations, including determining at least one field-related phase distribution of the at least one target.

These and other objects, features and advantages of the exemplary embodiment of the present disclosure will become apparent upon reading the following detailed description of the exemplary embodiments of the present disclosure, when taken in conjunction with the appended claim.

BRIEF DESCRIPTION OF THE DRAWINGS

Exemplary objects, features and advantages of the present disclosure will become apparent from the following detailed description taken in conjunction with the accompanying Figs. showing illustrative embodiments of the present disclosure, in which.

Figure 1:
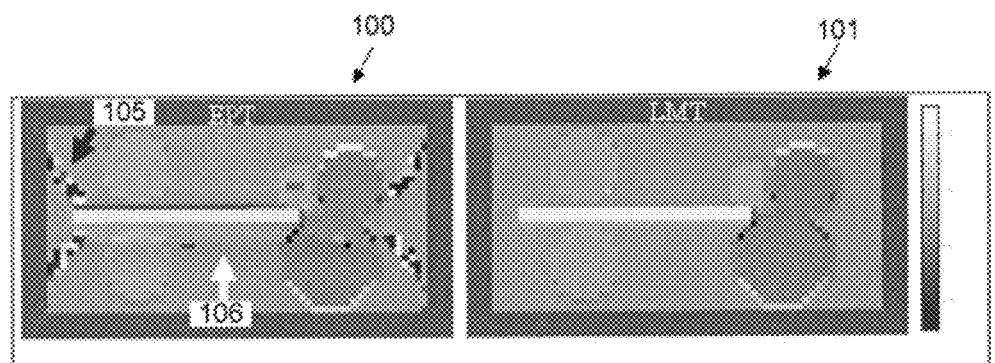
FIG. 1 shows exemplary numerical simulations of conductivity maps, according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures or the claims appended herewith.

DETAILED DESCRIPTION OF EXEMPLARY EMBODIMENTS

Exemplary embodiments of the present disclosure indicate that at least some of the distortions observed in magnetic resonance images can be used to provide a robust solution to the problem of electrical property mapping. It has long been recognized that the distribution of intensities in MR images obtained at high magnetic field strength, and correspondingly high Larmor frequency, reflects the shaping of radiofrequency (RF) fields by tissue, in addition to the underlying distribution of magnetization. The RF transmitter and detector coils used to generate and collect MR signals are known to be perturbed more and more strongly by body structure with increasing frequency, and various characteristic artifacts have been attributed to the interference of applied and induced RF fields in high-field MRI. The exemplary embodiments of the present disclosure demonstrates that certain calibration procedures sometimes used to characterize these artifacts, together with certain experimental and mathematical procedures, can be utilized to obtain all the information required for noncontact mapping of electrical permittivity and conductivity.

An exemplary embodiment of the Local Maxwell Tomography (LMT) technique according to the present disclosure that is described herein uses measurements of magnetic field curvature in arrays of RF transmitter and detector coils to deduce the underlying distribution of electrical properties via a well-posed local inverse problem free of symmetry assumptions and deductions regarding RF phase that have limited prior methods. The exemplary LMT can solve simultaneously for key functions of the missing RF phase distribution along with unknown electrical properties, e.g., using complementary information from the transmit and receive sensitivity distributions of multiple coils to resolve ambiguities. As a result, the exemplary LMT can facilitate an electrical property mapping at arbitrary field strength, with a wide range of coil designs, and free of errors associated with rapid field variation. LMT is a powerfully general approach, from which a wide range of useful special cases may be derived. The use of transmit and receive sensitivities together can be an important feature of the exemplary LMT, since it can be the conjugate relationship of transmit versus receive sensitivities to the missing RF reference phase which enables unique determination of that phase and hence of electrical property distributions.

Exemplary embodiments of the LMT procedure can include procedures involving data acquisition as well as image reconstruction. Data acquisition can include recording of signals received in a plurality of detectors from a plurality of excitations in a plurality of transmitters. Image reconstruction can include manipulation of measured data to generate quantities related to transmit and receive fields, followed by construction and then solution of systems of master equations relating the measured/generated field-related quantities to unknowns including the desired electrical properties. The theory underlying construction of exemplary LMT master equations will be described further below. A variety of possible methods of the exemplary solution of such master equations are also described in this disclosure, along with a variety of choices of coil designs and combinations, numerical derivative algorithms, and experimental procedures to improve the robustness of resulting electrical property maps.

Exemplary LMT master equations can be constructed using the following general procedure:
  a) Determine local expressions for the Maxwell equations (e.g., Helmholz equations for time-harmonic fields) relating field curvature to the electrical properties of interest.
  b) Express the true laboratory-frame magnetic fields as products or other combinations of measurable quantities (or quantities ultimately derivable from measurements) and residual unknowns. The unknowns can include the missing reference phase distribution as well as the unknown distribution of magnetization and other signal variation not associated with electrodynamics.
  c) Insert these composite expressions into the local Maxwell equations, and use the product law of differentiation, for example, to separate terms associated with measurable quantities from those associated with unknowns.
  d) Group terms to form a system of equations in which the known coefficients represent various local derivatives of measurable quantities, and the unknowns include local derivatives of the unknown phase and magnetization distributions, as well as the local values of electrical properties.

Use of local derivatives as coefficients and unknowns in this exemplary procedure can eliminate the need to address boundary conditions explicitly, avoiding the spatiotemporal coupling typical of Maxwell equations and accounting for the locality of LMT. The tomographic character of the exemplary LMT technique can be provided in the following exemplary characteristics: (1) the use of volumetric tomographic MR data to bypass the ill-posed inverse problem associated with electrical prospection using surface-derived measurements, and (2) the use of complementary data from multiple transmit and receive coils to fix many or all unknown quantities, including those associated with missing phase and magnetization distributions.

Exemplary solutions of the exemplary LMT master equations can use any of a number of linear or nonlinear methods known in the art to determine values of the unknown quantities. Exemplary solutions can be provided through the use of a sufficient number of appropriately designed transmitter coils balanced against a sufficient number of suitably designed detector coils Following a general derivation of the exemplary LMT formalism and its master equations, this disclosure demonstrates several possible strategies for solution of these equations. It then illustrates that EPT can be derived as a special case of LMT under the assumption that the missing phase is known. Other simplified cases for tailored reconstruction can also be derived from the full LMT formalism, and selected examples are provided. Certain exemplary procedures for the robust exemplary LMT data acquisition and image reconstruction are described herein.

General derivation of exemplary LMT formalism and master equations: The derivations that follow can assume time-harmonically driven electric and magnetic fields E(r,t) and B(r,t) of the following form:

$$E(r,t) = E(r)\exp(-i\omega t)$$

$$B(r,t) = B(r)\exp(-i\omega t) \quad (1)$$

For example, ω is the angular frequency of the Larmor frequency drive and r represents spatial coordinates in the laboratory frame. Traditional derivations of the Helmholtz equation take the curl of both sides of the differential form of Ampere's Law:

$$\nabla \times \{\nabla \times B\} = \nabla(\underbrace{\nabla \cdot B}_{0}) - \nabla^2 B \quad (2)$$

$$= \nabla \times \left\{\mu\left(J + \frac{\partial D}{\partial t}\right)\right\}$$

$$= \nabla \times \{\mu(\sigma - i\omega\varepsilon)E\}$$

$$= \mu(\sigma - i\omega\varepsilon)\nabla \times E + \nabla\{\mu(\sigma - i\omega\varepsilon)\} \times E$$

$$= i\omega\mu(\sigma - i\omega\varepsilon)B + \nabla\{\mu(\sigma - i\omega\varepsilon)\} \times E$$

In Eq. (2), the ohmic relation J=σE has been applied, the electrical conductivity has been denoted as σ, the electric permittivity as ∈, and the magnetic permeability as μ. For the moment, σ, ∈, and μ are assumed to be scalar functions of position r, though their generalization to tensor quantities is also possible within the exemplary LMT formalism. For exemplary biomedical applications, variations in μ can be sufficiently small with respect to variations in σ and ∈ that they may safely be ignored. The exemplary result can be an equation (e.g., the usual Helmholtz equation modified by a gradient term in the case of inhomogeneous electromagnetic properties) which relates the curvature of electromagnetic fields to the local values of electromagnetic properties:

$$\nabla^2 B = -i\omega\mu(\sigma - i\omega\in)B - \nabla\{\mu(\sigma - i\omega\in)\} \times E \quad (3)$$

Eq. (3) may be insufficient to specify the precise functional form of electromagnetic fields in the absence of information on boundary conditions; however, if sufficient information is available about the structure of the fields, the electrical properties may be deduced even in the absence of boundary condition information. In particular, for piecewise constant electrical properties and/or for property gradients suitably aligned with respect to the local electric field, $(\nabla\{\mu(\sigma-i\omega\varepsilon)\}\times E)_\alpha \to 0$, and a Helmholtz relation holds for any component $B_\alpha$ of the vector magnetic field:

$$\nabla^2 B_\alpha \approx -i\omega\mu(\sigma-i\omega\varepsilon)B_\alpha \qquad (4)$$

The exemplary transmit and receive sensitivities of RF coils in MRI can be known to reflect the distribution of transverse magnetic field components $B_x \pm iB_y$. If the true amplitude and phase of these field components were known from MRI experiments, it would be possible to compute electrical properties directly from Eq. (4) alone. However, MRI techniques may not provide direct access to pure laboratory-frame field values. Instead, it can measure indirect quantities, depending upon the choice of pulse sequence, transmit and receive coil configuration, and image post-processing algorithm. For example, while the amplitude $|B_x+iB_y|$ may be determined using flip angle mapping procedures, however, the absolute phase of transverse RF magnetic field components has until now been considered fundamentally inaccessible to experiment. On the way from a transmitter to any body region of interest, the phase of the local RF excitation field deviates from the phase of the driving field as a result of varying propagation delays, as well as other perturbations due to the body's particular distribution of electrical properties. Likewise, the phase of the field produced by a precessing spin suffers various perturbations on its way back to a detector. Even if the transmitter and the detector share the same structure and position, the perturbations in each of these directions are not equivalent, particularly as operating frequency increases, as a result of the circularly polarized nature of the exemplary MR signal. Since the exemplary MR experiments can involve some combination of signal generation and signal detection, any measured phase reflects a combination of sources. In other words, there may be no absolute "clock" for MR signal phase. Any measured distribution is referenced to another distribution that cannot be measure. In most applications of MRI, knowledge of relative phase suffices. Nevertheless, accurate solution of Eq. (4) can indicate that phase be specified absolutely, at least up to an overall constant, or else error terms will result from the derivatives on the left hand side operating on the unknown reference phase distribution $\phi_0(r)$:

$$\nabla^2 \{B_\alpha(r)\exp(i\phi_0(r))\} = -i\omega\mu(\sigma-i\omega\varepsilon)\{B_\alpha(r)\exp(i\phi_0(r))\} + \qquad (5)$$
$$2\nabla B_\alpha(r) \cdot \nabla \exp(i\phi_0(r)) + B_\alpha(r)\nabla^2 \exp(i\phi_0(r))$$

Exemplary embodiments of the present disclosure can demonstrate that a solution to the problem of unknown reference phase can be derived by exploiting the complementarity of transmit and receive sensitivities. As described herein in detail, transmit and receive fields can have a conjugate relationship to any particular choice of reference phase $\phi_0(r)$, and, in the setting of a sufficient number of coils, this relationship can resolve the phase ambiguity which was previously considered intractable.

For a general array of L transmit coils and L' receive coils, spatial distributions of the following exemplary quantities can be determined:

First, an MR signal $S_{l,l'}$ from transmit coil l and receive coil l':

$$S_{l,l'} = Mf(|B_{1,l}^{(+)}|)\frac{B_{1,l}^{(+)}}{|B_{1,l}^{(+)}|}B_{1,l'}^{(-)} \qquad (6)$$

$$\equiv |M|f(|B_{1,l}^{(+)}|)|B_{1,l'}^{(-)}|\exp\left(i\left(\varphi_{B_{1,l}^{(+)}} + \varphi_{B_{1,l'}^{(-)}} + \varphi_M\right)\right)$$

For example, the function M incorporates all sources of signal variation that are common to all coils and that are not associated with electrodynamics. This can include the spatial distribution of equilibrium magnetization, as well as all non-electrodynamic phase variation $\phi_M$, e.g., due to $B_0$ inhomogeneity, gradient eddy currents, incomplete RF spoiling, etc. Eq. (6) uses the field definitions $B_{1,l}^{(\pm)} \equiv B_{x,l} \pm iB_{y,l}$, relating transmit or receive sensitivity patterns to the complex laboratory-frame transverse magnetic field components $B_{x,l}$ and $B_{y,l}$ generated by a unit current in coil 1. The phases $\phi_{B_{1,l}^{(+)}}$ and $\phi_{B_{1,l}^{(-)}}$ define the flip axis of the transmit coil l and the reference phase of the receive coil l', respectively. The function $f(|B_{1,l}^{(+)}|)$ depends upon details of the pulse sequence used for data acquisition. For a simple exemplary gradient-echo sequence with long TR, $f(|B_{1,l}^{(+)}|) \approx -i\omega \sin(\gamma I |B_{1,l}^{(+)}|\tau)/2$, where $\gamma$ is the gyromagnetic ratio, I is the current applied to the transmit coil, and $\tau$ is the pulse duration. In the limit of small flip angle, Eq. (6) then simplifies to, $S_{l,l'} \approx -i\omega\gamma\tau IMB_{1,l}^{(+)}B_{1,l'}^{(-)}/2$.

Second, a transmit field amplitude map for transmit coil l, from a flip angle mapping experiment:

$$|B_{1,l}^{(+)}| \qquad (7)$$

Third, an exemplary phase map for the function M, e.g. from a $B_0$ mapping experiment, perhaps with gradient eddy current compensation:

$$\phi_M \qquad (8)$$

From these three basic measurable quantities, exemplary embodiments can construct various relationships among field quantities of interest. For example, knowing $|B_{1,l}^{(+)}|$ and the functional form of f appropriate to the pulse sequence used, Eq. (6) may be divided by $f(|B_{1,l}^{(+)}|)$ and the absolute magnitude taken to yield the spatial distribution of the quantity $|MB_{1,l'}^{(-)}|$. In addition, by determining and/or computing the phase angle of the MR signal in Eq. (6), and correcting for any background phase $\phi_M$, the following sum of field phases may be derived for any transmit-receive coil pair:

$$\phi_{B_{1,l}^{(+)}} + \phi_{B_{1,l'}^{(-)}} \qquad (9)$$

By taking ratios of signals between distinct transmit or receive coils, relative transmit or receive field phases can also be derived:

$$\left(\varphi_{B_{1,l}^{(+)}} + \varphi_{B_{1,l'}^{(-)}}\right) - \left(\varphi_{B_{1,m}^{(+)}} + \varphi_{B_{1,l'}^{(-)}}\right) = \left(\varphi_{B_{1,l}^{(+)}} + \varphi_{B_{1,m}^{(+)}}\right) \qquad (10)$$

$$\left(\varphi_{B_{1,l}^{(+)}} + \varphi_{B_{1,l'}^{(-)}}\right) - \left(\varphi_{B_{1,l}^{(+)}} + \varphi_{B_{1,m'}^{(-)}}\right) = \left(\varphi_{B_{1,l'}^{(-)}} - \varphi_{B_{1,m'}^{(-)}}\right)$$

None of these phase relations can be sufficient to determine the absolute phase of any individual transmit or receive field. Using the sum and difference relations in Eq.'s (9) and (10), all phases can ultimately be expressed in relation to a single unknown phase distribution—for example, the transmit or receive phase distribution of a single reference coil. However, there is no straightforward means of determining that missing reference phase distribution. This is a mathematical manifestation of the problem of absolute RF phase determination.

In the exemplary LMT, fundamental conjugate relations between transmit and receive fields can be used to solve directly for key functions of the unknown reference phase, simultaneously with the unknown electrical property distributions. LMT master equations can be derived by expressing true field components as products of measurables with unknown quantities, e.g.:

$$B_{1,l}^{(+)} = \underbrace{\left(|B_{1,l}^{(+)}|\exp\left(i\left(\varphi_{B_{1,l}^{(+)}} + \varphi_{B_{1,l_0}^{(-)}}\right)\right)\right)}_{known}\underbrace{\left(\exp\left(-i\varphi_{B_{1,l_0}^{(-)}}\right)\right)}_{unknown} \tag{11}$$

$$\equiv \underbrace{(|B_{1,l}^{(+)}|\exp(i\varphi_{\Sigma_l}))}_{known}\underbrace{(\exp(-i\varphi_0))}_{unknown}$$

$$B_{1,l'}^{(-)} = \underbrace{\left(|MB_{1,l'}^{(-)}|\exp\left(i\left(\varphi_{B_{1,l'}^{(-)}} - \varphi_{B_{1,l_0}^{(-)}}\right)\right)\right)}_{known}\underbrace{\left(\frac{1}{|M|}\exp\left(+i\varphi_{B_{1,l_0}^{(-)}}\right)\right)}_{unknown} \tag{12}$$

$$\equiv \underbrace{(|MB_{1,l'}^{(-)}|\exp(i\varphi_{\Delta_{l'}}))}_{known}\underbrace{\left(\frac{1}{M}\exp(+i\varphi_0)\right)}_{unknown}$$

Such quantities can be defined with respect to the unknown phase distribution $\phi_0$ of a common reference receive coil $l_0$, but any coil combination can also serve as a legitimate phase reference.

Plugging Eq. (11) into Eq. 12 and applying the product rule for differentiation yields the following relation:

$$\frac{\nabla^2 B_{1,l}^{(+)}}{B_{1,l}^{(+)}} \approx -i\omega\mu(\sigma - i\omega\varepsilon) \tag{13}$$

$$= -\omega^2\mu\varepsilon - i\omega\mu\sigma$$

$$= \frac{\nabla^2(|B_{1,l}^{(+)}|\exp(i(\varphi_{\Sigma_l} - \varphi_0)))}{|B_{1,l}^{(+)}|\exp(i(\varphi_{\Sigma_l} - \varphi_0))}$$

$$= \frac{\nabla^2|B_{1,l}^{(+)}|}{|B_{1,l}^{(+)}|} + \frac{2\nabla|B_{1,l}^{(+)}|\cdot\nabla\exp(i(\varphi_{\Sigma_l} - \varphi_0))}{|B_{1,l}^{(+)}|\exp(i(\varphi_{\Sigma_l} - \varphi_0))} +$$

$$\frac{\nabla^2\exp(i(\varphi_{\Sigma_l} - \varphi_0))}{\exp(i(\varphi_{\Sigma_l} - \varphi_0))}$$

Using the following expressions for first and second derivatives $$\frac{\nabla\exp(\pm i\varphi)}{\exp(\pm i\varphi)} = \pm i\nabla\varphi \tag{14}$$

$$\frac{\nabla^2\exp(\pm i\varphi)}{\exp(\pm i\varphi)} = \frac{\nabla\cdot\nabla\exp(\pm i\varphi)}{\exp(\pm i\varphi)}$$

$$= \frac{\nabla\cdot(\pm i\exp(\pm i\varphi)\nabla\varphi_0)}{\exp(\pm i\varphi)}$$

$$= -\nabla\varphi\cdot\nabla\varphi \pm i\nabla^2\varphi$$

and making the substitution $\nabla|B_{1,l}^{(+)}|/|B_{1,l}^{(+)}|=\nabla\ln|B_{1,l}^{(+)}|$, Eq. (13) can be expanded in real and imaginary components, yielding the following exemplary master equations relating known and unknown transmit field quantities to electrical properties at each spatial position independently:

$$2\nabla\varphi_{\Sigma_l}\cdot\nabla\varphi_0 - \nabla\varphi_0\cdot\nabla\varphi_0 + \left(\frac{\nabla^2|B_{1,l}^{(+)}|}{|B_{1,l}^{(+)}|} - \nabla\varphi_{\Sigma_l}\cdot\nabla\varphi_{\Sigma_l}\right) = -\omega^2\mu\varepsilon \tag{15}$$

$$-2\nabla\ln|B_{1,l}^{(+)}|\cdot\nabla\varphi_0 - \nabla^2\varphi_0 + (2\nabla\ln|B_{1,l}^{(+)}|\cdot\nabla\varphi_{\Sigma_l} + \nabla^2\varphi_{\Sigma_l}) = -\omega\mu\sigma$$

A similar treatment of Eq. (12) yields the following exemplary master equations for receive fields:

$$\left\{\begin{array}{l} -2\nabla\varphi_{\Delta_{l'}}\cdot\nabla\varphi_0 - \nabla\varphi_0\cdot\nabla\varphi_0 - 2\nabla\ln|MB_{1,l'}^{(-)}|\cdot\nabla\ln|M| + \dfrac{\nabla^2|M|^{-1}}{|M|^{-1}} + \\ \left(\dfrac{\nabla^2|MB_{1,l'}^{(-)}|}{|MB_{1,l'}^{(-)}|} - \nabla\varphi_{\Delta_{l'}}\cdot\nabla\varphi_{\Delta_{l'}}\right) \end{array}\right\} = \tag{16}$$

$$-\omega^2\mu\varepsilon$$

$$\left\{\begin{array}{l} 2\nabla\ln|MB_{1,l'}^{(-)}|\cdot\nabla\varphi_0 + \nabla^2\varphi_0 - 2\nabla\varphi_{\Delta_{l'}}\cdot\nabla\ln|M| - 2\nabla\varphi_0\cdot\nabla\ln|M| + \\ (2\nabla\ln|MB_{1,l'}^{(-)}|\cdot\nabla\varphi_{\Delta_{l'}} + \nabla^2\varphi_{\Delta_{l'}}) \end{array}\right\} =$$

$$-\omega\mu\sigma$$

Grouping all known quantities and unknown quantities, and rewriting in matrix form:

$$\underbrace{\begin{bmatrix} A_{11}^{(l)} & A_{12}^{(l)} & A_{13}^{(l)} & 1 & 0 & 0 & 0 & 0 & 0 & 1 & 0 \\ A_{21}^{(l)} & A_{22}^{(l)} & A_{23}^{(l)} & 0 & -1 & 0 & 0 & 0 & 0 & 0 & 1 \\ A_{31}^{(l')} & A_{32}^{(l')} & A_{33}^{(l')} & 1 & 0 & -A_{41}^{(l')} & -A_{42}^{(l')} & -A_{43}^{(l')} & 1 & 0 & 1 & 0 \\ A_{41}^{(l')} & A_{42}^{(l')} & A_{43}^{(l')} & 0 & 1 & A_{31}^{(l')} & A_{32}^{(l')} & A_{33}^{(l')} & 0 & -1 & 0 & 1 \end{bmatrix}}_{A} \tag{17}$$

$$\underbrace{\begin{bmatrix} \frac{\partial\varphi_0}{\partial x} \\ \frac{\partial\varphi_0}{\partial y} \\ \frac{\partial\varphi_0}{\partial z} \\ -\nabla\varphi_0\cdot\nabla\varphi_0 \\ \nabla^2\varphi_0 \\ \frac{\partial\ln|M|}{\partial x} \\ \frac{\partial\ln|M|}{\partial y} \\ \frac{\partial\ln|M|}{\partial z} \\ \frac{\nabla^2|M|^{-1}}{|M|^{-1}} \\ 2\nabla\varphi_0\cdot\nabla\ln|M| \\ \omega^2\mu\varepsilon \\ \omega\mu\sigma \end{bmatrix}}_{x} = \underbrace{\begin{bmatrix} b_1^{(l)} \\ b_2^{(l)} \\ b_3^{(l')} \\ b_4^{(l')} \end{bmatrix}}_{b}$$

The following matrix and vector element definitions apply in Eq. (17):

$$A_{11}^{(l)} = \frac{2\partial \varphi_{\Sigma_l}}{\partial x} \quad A_{12}^{(l)} = \frac{2\partial \varphi_{\Sigma_l}}{\partial y} \quad A_{13}^{(l)} = \frac{2\partial \varphi_{\Sigma_l}}{\partial z} \tag{18}$$

$$A_{21}^{(l)} = \frac{-2\partial \ln|B_{1,l}^{(+)}|}{\partial x} \quad A_{22}^{(l)} = \frac{-2\partial \ln|B_{1,l}^{(+)}|}{\partial y} \quad A_{23}^{(l)} = \frac{-2\partial \ln|B_{1,l}^{(+)}|}{\partial z}$$

$$A_{31}^{(l')} = \frac{-2\partial \varphi_{\Delta_{l'}}}{\partial x} \quad A_{32}^{(l')} = \frac{-2\partial \varphi_{\Delta_{l'}}}{\partial y} \quad A_{33}^{(l')} = \frac{-2\partial \varphi_{\Delta_{l'}}}{\partial z}$$

$$A_{41}^{(l')} = \frac{2\partial \ln|MB_{1,l'}^{(-)}|}{\partial x} \quad A_{42}^{(l')} = \frac{2\partial \ln|MB_{1,l'}^{(-)}|}{\partial y} \quad A_{43}^{(l')} = \frac{2\partial \ln|MB_{1,l'}^{(-)}|}{\partial z}$$

$$b_1^{(l)} = \frac{-\nabla^2 |B_{1,l}^{(+)}|}{|B_{1,l}^{(+)}|} + \nabla \varphi_{\Sigma_l} \cdot \nabla \varphi_{\Sigma_l}$$

$$b_2^{(l)} = -2\nabla \ln|B_{1,l}^{(+)}| \cdot \nabla \varphi_{\Sigma_l} - \nabla^2 \varphi_{\Sigma_l}$$

$$b_3^{(l')} = \frac{-\nabla^2 |MB_{1,l'}^{(-)}|}{|MB_{1,l'}^{(-)}|} + \nabla \varphi_{\Delta_{l'}} \cdot \nabla \varphi_{\Delta_{l'}}$$

$$b_4^{(l')} = -2\nabla \ln|MB_{1,l'}^{(-)}| \cdot \nabla \varphi_{\Delta_{l'}} - \nabla^2 \varphi_{\Delta_{l'}}$$

The exemplary embodiment of the system of matrix equations according to the present disclosure can be composed of concatenated blocks of the form of Eq. (17), with one block resembling the top two rows for each transmit coil l, and one block resembling the bottom two rows for each receive coil l'. Equations involving transmit coils alone or receive coils alone do not have unique solutions, whereas a suitable balance of transmit and receive coils can have a unique solution.

Eq. (17) takes the general form of a linear system of equations Ax=b. For example, the relationships among the elements of the unknown vector x in Eq. (17) deviate from linearity, namely:

$$x_4 = -(x_1^2 + x_2^2 + x_3^2)$$

$$x_{10} = 2(x_1 x_6 + x_2 x_7 + x_3 x_8) \tag{19}$$

Eq. (17) can thus represent a "nearly" linear system of 2(L+L') real equations with 10 real unknowns. The unknowns can include the missing permittivity and conductivity at any chosen local position, as well as the local values of first and second derivatives of the missing reference phase and common magnetization distribution. If the local derivatives in the matrix A can be computed reliably from measured quantities, then the exemplary LMT master questions can also be local, and may be solved voxel by voxel in parallel.

Strategies for solution of the LMT master equations: The exemplary LMT master equations such as those defined in Eq. (17) may be solved in a variety of ways. Exemplary embodiments of various solution strategies are described to follow. A wide range of other techniques can also be applied by those skilled in the art once the fundamental master equations have been correctly formulated.

Simplified two-step exemplary linear solution: For the special case of a locally uniform (i.e., piecewise constant or slowly varying) magnetization distribution, Eq. (17) takes the following simplified form:

$$\underbrace{\begin{bmatrix} A_{11}^{(l)} & A_{12}^{(l)} & A_{13}^{(l)} & 0 & 1 & 0 \\ A_{21}^{(l)} & A_{22}^{(l)} & A_{23}^{(l)} & -1 & 0 & 1 \\ A_{31}^{(l')} & A_{32}^{(l')} & A_{33}^{(l')} & 0 & 1 & 0 \\ A_{41}^{(l')} & A_{42}^{(l')} & A_{43}^{(l')} & 1 & 0 & 1 \end{bmatrix}}_{\tilde{A}} \underbrace{\begin{bmatrix} \frac{\partial \varphi_0}{\partial x} \\ \frac{\partial \varphi_0}{\partial y} \\ \frac{\partial \varphi_0}{\partial z} \\ \nabla^2 \varphi_0 \\ \omega^2 \mu \varepsilon \\ \omega \mu \sigma \end{bmatrix}}_{\tilde{x}} \overset{|M|=const}{=} \underbrace{\begin{bmatrix} b_1^{(l)} + \nabla \varphi_0 \cdot \nabla \varphi_0 \\ b_2^{(l)} \\ b_3^{(l')} + \nabla \varphi_0 \cdot \nabla \varphi_0 \\ b_4^{(l')} \end{bmatrix}}_{\tilde{b}} \tag{20}$$

This exemplary equation can be solved directly with a nonlinear optimization algorithm of choice. Alternatively, the equations for conductivity and permittivity can be separated into two sets of equations sharing some of the same unknowns:

$$\underbrace{\begin{bmatrix} A_{21}^{(l)} & A_{22}^{(l)} & A_{23}^{(l)} & -1 & 1 \\ A_{41}^{(l')} & A_{42}^{(l')} & A_{43}^{(l')} & 1 & 1 \end{bmatrix}}_{\tilde{A}^{(\sigma)}} \underbrace{\begin{bmatrix} \frac{\partial \varphi_0}{\partial x} \\ \frac{\partial \varphi_0}{\partial y} \\ \frac{\partial \varphi_0}{\partial z} \\ \nabla^2 \varphi_0 \\ \omega \mu \sigma \end{bmatrix}}_{\tilde{x}^{(\sigma)}} \overset{|M|=const}{=} \underbrace{\begin{bmatrix} b_2^{(l)} \\ b_4^{(l')} \end{bmatrix}}_{\tilde{b}^{(\sigma)}} \tag{21}$$

$$\underbrace{\begin{bmatrix} A_{11}^{(l)} & A_{12}^{(l)} & A_{13}^{(l)} & 1 \\ A_{31}^{(l')} & A_{32}^{(l')} & A_{33}^{(l')} & 1 \end{bmatrix}}_{\tilde{A}^{(\varepsilon)}} \underbrace{\begin{bmatrix} \frac{\partial \varphi_0}{\partial x} \\ \frac{\partial \varphi_0}{\partial y} \\ \frac{\partial \varphi_0}{\partial z} \\ \omega^2 \mu \varepsilon \end{bmatrix}}_{\tilde{x}^{(\varepsilon)}} \overset{|M|=const}{=} \underbrace{\begin{bmatrix} b_1^{(l)} + \nabla \varphi_0 \cdot \nabla \varphi_0 \\ b_3^{(l')} + \nabla \varphi_0 \cdot \nabla \varphi_0 \end{bmatrix}}_{\tilde{b}^{(\varepsilon)}} \tag{22}$$

Eq. (21) is a purely linear equation, and can be solved in a least-squares sense, for example using a Moore-Penrose inverse of the matrix $\tilde{A}^{(\sigma)}$:

$$\tilde{x}^{(\sigma)} = [(\tilde{A}^{(\sigma)})^T (\tilde{\Psi}^{(\sigma)})^{-1} \tilde{A}^{(\sigma)}]^{-1} (\tilde{A}^{(\sigma)})^T (\tilde{\Psi}^{(\sigma)})^{-1} \tilde{b}^{(\sigma)} \tag{23}$$

For example, $\tilde{\Psi}^{(\sigma)}$ is an optional noise/error covariance matrix which will be further discussed below, and can provide the weighting and noise decorrelation required for an optimal solution in the presence of noise and error. Standard matrix conditioning strategies can also be used in this inversion. One simple conditioning strategy is to scale the unit elements of $\tilde{A}^{(\sigma)}$ to match the average value of the other elements, and to scale the corresponding unknown elements of $\tilde{x}^{(o)}$ to preserve the product. In practice, this balancing strategy can significantly improve performance. More advanced regularization strategies, such as Tikhonov regularization, can also be employed.

Both transmit and receive elements can be used to render $\tilde{A}^{(o)}$ as defined in Eq. (21) nonsingular. This reflects the fact that, for transmit or receive coils only, the coefficients of the unknown terms $\nabla^2 \phi_0$ and $\omega\mu\sigma$ are coil-independent. Therefore, according to one exemplary embodiment, for transmit or receive coils only, values of $\nabla^2 \phi_0$ and $\omega\mu\sigma$ may be interchanged freely as long as their sum or difference is preserved, and there is no unique solution. However, the opposite sign of the coefficient of $\nabla^2 \phi_0$ for transmit as opposed to receive coils can resolve this ambiguity, and uniquely fixes all unknowns. In other words, it is the opposite sign of the reference phase between transmit and receive that can ultimately fix the missing phase which has long plagued electrical property mapping from MR field data. Any deviation from truth in a candidate value of $\nabla^2 \phi_0$ in a transmit equation can result in an oppositely-directed deviation in any of the receive equations, and consistency among equations is spoiled.

When Eq. (21) has been solved and the values of $\nabla \phi_0$ are known, these values can be inserted into Eq. (22) and the known quantities grouped on the right hand side to yield the solution $$\begin{bmatrix} 1 \\ 1 \end{bmatrix} \overbrace{[\omega^2 \mu \varepsilon]}^{\tilde{x}^{(\varepsilon)}}_{|M|=const} = \overbrace{\begin{bmatrix} b_1^{(l)} + \nabla\varphi_0 \cdot \nabla\varphi_0 - 2\nabla\varphi_{\Sigma_l} \cdot \nabla\varphi_0 \\ b_3^{(l')} + \nabla\varphi_0 \cdot \nabla\varphi_0 + 2\nabla\varphi_{\Delta_{l'}} \cdot \nabla\varphi_0 \end{bmatrix}}^{\tilde{b}^{(\varepsilon)}} \quad (24)$$

The mean or another suitable weighted average of the resulting coil-by-coil estimates of $\in$ can then be taken to derive a single best-fit estimate.

This exemplary two-stage linear reconstruction strategy can be extremely fast. It also serves to demonstrate requirements for a robust solution of the electrical property mapping problem. As one example, a total of at least five field maps, taken from at least one transmit and at least one receive coil, is required to fix the values of the five unknowns in Eq. (21). The same five coil dataset suffices to solve Eq. (24). Receive coils can also share the same structure as transmit coils, if the array is operated in transmit-receive mode. Thus, a 3-element transmit-receive array is sufficient to determine both $\sigma$ and $\in$. The conditioning of the problem generally improves as the number of independent coils increases, and also as the number of transmit coils is balanced against the number of receive coils. Otherwise, the condition number of the matrix $\tilde{A}^{(o)}$ depends upon the balance of the relevant gradients of measured field amplitudes and phases, which in turn depends upon the design of the transmit and receive coil array/s.

Full nonlinear solution: Returning to the case of non-constant magnetization distribution, Eq. (17) can be rewritten, separating out the true unknowns and formulating a nonlinear search problem:

$$\overbrace{\begin{bmatrix} A_{11}^{(l)} & A_{12}^{(l)} & A_{13}^{(l)} & 0 & 0 & 0 & 0 & 0 & 1 & 0 \\ A_{21}^{(l)} & A_{22}^{(l)} & A_{23}^{(l)} & -1 & 0 & 0 & 0 & 0 & 0 & 1 \\ A_{31}^{(l')} & A_{32}^{(l')} & A_{33}^{(l')} & 0 & -A_{41}^{(l')} & -A_{42}^{(l')} & -A_{43}^{(l')} & 1 & 1 & 0 \\ A_{41}^{(l')} & A_{42}^{(l')} & A_{43}^{(l')} & 1 & A_{31}^{(l')} & A_{32}^{(l')} & A_{33}^{(l')} & 0 & 0 & 1 \end{bmatrix}}^{\tilde{A}^{(M)}} \quad (25)$$

$$\overbrace{\begin{bmatrix} \partial\varphi_0/\partial x \\ \partial\varphi_0/\partial y \\ \partial\varphi_0/\partial z \\ \nabla^2 \varphi_0 \\ \partial\ln|M|/\partial x \\ \partial\ln|M|/\partial y \\ \partial\ln|M|/\partial z \\ \nabla^2 |M|^{-1} \\ |M|^{-1} \\ \omega^2 \mu\varepsilon \\ \omega\mu\sigma \end{bmatrix}}^{\tilde{x}^{(M)}} = \overbrace{\begin{bmatrix} b_1^{(l)} + \nabla\varphi_0 \cdot \nabla\varphi_0 \\ b_2^{(l)} \\ b_3^{(l')} + \nabla\varphi_0 \cdot \nabla\varphi_0 \\ b_4^{(l')} - 2\nabla\varphi_0 \cdot \nabla\ln|M| \end{bmatrix}}^{\tilde{b}^{(M)}}$$

This can be treated as a single nonlinear optimization problem, e.g. minimizing $\|A^{(M)}x^{(M)} - b^{(M)}\|_2$. Alternatively it can be divided once again into two coupled problems, as follows:

$$\overbrace{\begin{bmatrix} A_{21}^{(l)} & A_{22}^{(l)} & A_{23}^{(l)} & -1 & 0 & 0 & 0 & 1 \\ A_{41}^{(l')} & A_{42}^{(l')} & A_{43}^{(l')} & 1 & A_{31}^{(l')} & A_{32}^{(l')} & A_{33}^{(l')} & 1 \end{bmatrix}}^{\tilde{A}^{(M,\sigma)}} \overbrace{\begin{bmatrix} \partial\varphi_0/\partial x \\ \partial\varphi_0/\partial y \\ \partial\varphi_0/\partial z \\ \nabla^2 \varphi_0 \\ \partial\ln|M|/\partial x \\ \partial\ln|M|/\partial y \\ \partial\ln|M|/\partial z \\ \omega\mu\sigma \end{bmatrix}}^{\tilde{x}^{(M,\sigma)}} = \quad (26)$$

$$\overbrace{\begin{bmatrix} b_2^{(l)} \\ b_4^{(l')} - 2\nabla\varphi_0 \cdot \nabla\ln|M| \end{bmatrix}}^{\tilde{b}^{(M,\sigma)}}$$

Eq. (26) resembles Eq. (21), with the addition of three new unknowns and corresponding matrix coefficients for receive equations on the left-hand side, and with a single nonlinear receive term on the right hand side. This can be solved using nonlinear optimization to minimize a quantity such as $\|\tilde{A}^{(M,o)}\tilde{x}^{(M,o)} - \tilde{b}^{(M,o)}\|_2$. Once the values of $\nabla\phi_0$ and $\nabla\ln|M|$ are known, the remaining equations for $\in$ can be rewritten as follows:

$$\begin{bmatrix} 0 & 1 \\ 1 & 1 \end{bmatrix} \overbrace{\begin{bmatrix} \nabla^2 |M|^{-1} \\ |M|^{-1} \\ \omega^2 \mu \varepsilon \end{bmatrix}}^{\hat{x}^{(M,\varepsilon)}} = \overbrace{\begin{bmatrix} b_1^{(l)} + \nabla \varphi_0 \cdot \nabla \varphi_0 - 2\nabla \varphi_{\Sigma_l} \cdot \nabla \varphi_0 \\ b_3^{(l')} + \nabla \varphi_0 \cdot \nabla \varphi_0 + 2\nabla \varphi_{\Delta_{l'}} \cdot \\ \nabla \varphi_0 + 2\nabla \ln |MB_{1-l'}| \cdot \nabla \ln |M| \end{bmatrix}}^{\tilde{b}^{(M,\varepsilon)}} \quad (27)$$

In other words, once Eq. (26) has been solved, the solution for $\in$ is can again be trivial, and need not involve the magnetization gradients at all. The additional quantity $\nabla^2|M|^{-1}/|M|^{-1}$ is an optional parameter, which does not affect the value of $\in$ but may be solved knowing $\in$ along with $\nabla\phi_0$ and $\nabla \ln|M|$.

Exemplary Noise/error-optimized solution: Deviations from truth in the estimates of conductivity and permittivity derived by LMT may result from errors in the elements of the encoding matrix A and of the right hand side vector b, which, as can be seen from Eq. (18), involve local derivatives of field-related quantities. An exemplary computation of derivatives from noisy and error-prone measured spatial distributions can involve both amplification of underlying noise and potential systematic error. It may be observed that the right hand side vector b is composed of second derivatives or products of first derivatives, whereas the elements of A involve only first derivatives. Since higher-order derivatives are generally significantly more error-prone than lower-order derivatives (a fact verified experimentally for MR-derived field maps), and since the condition number of the encoding matrix A is generally smaller than the relative scaling between first and second derivatives, approximate expressions for noise and error propagation may be derived by neglecting errors in A:

$$\hat{x} = A^{-1}b = A^{-1}(b_0 + \Delta b) = (A_0^{-1} + \Delta(A^{-1}))b_0 + A^{-1}\Delta b \quad (28)$$

$$\xrightarrow{\Delta(A^{-1})b_0 < A^{-1}\Delta b} A_0^{-1}b_0 + A^{-1}\Delta b \equiv x_0 + \Delta x$$

For example, $\hat{x}$ is the reconstructed estimate of the unknown vector x, quantities labeled with a subscript 0 represent the true values of those quantities, quantities preceded by a $\Delta$ represent errors (random and/or systematic) in those quantities, and $A^{-1}$ represents the computed reconstruction matrix which inverts the effects of the encoding matrix A. This exemplary simplified error model bears a direct analogy to traditional error propagation analyses in parallel MR imaging or similar inverse problems, in which the dominant errors are generally taken to result from noise in the measured signal vector on the right hand side. According to this exemplary model, if a suitable noise covariance matrix $\Psi$ reflecting the distribution and correlation of noise among elements of the vector $\Delta b$ is defined, a signal-to-noise ratio (SNR) optimizing reconstruction may take the form of Eq. (23), e.g., $A^{-1}[A^T\Psi^{-1}A]^{-1}A^T\Psi^{-1}$. In that case, the SNR of any component k of the reconstructed vector $\hat{x}$, accounting for amplification of noise in the reconstruction, is $$SNR(\hat{x}_k) = \frac{\hat{x}_k}{(A^{-1}\Psi(A^{-1})^T)_{kk}^{1/2}} = \frac{\hat{x}_k}{([A^T\Psi^{-1}A]_{kk}^{-1})^{1/2}} \quad (29)$$

An exemplary noise covariance matrix for two-stage reconstruction according to Eqs. (21)-(24) can be formulated using partial derivatives with respect to each measured quantity according to standard error-propagation approaches. Since there are several nonlinear steps involved both in the mapping of $|B_1^{(+)}|$ and $|MB_1^{(-)}|$ and in the determination of the phases $\phi_\Sigma$ and $\phi_\Delta$ from raw MR signals, the resulting noise statistics may not be Gaussian, but the general propagation of noise remains calculable. An exemplary systematic error, as opposed to error resulting from random fluctuations, can also be included within the framework of a generalized covariance matrix.

A choice of $\Psi$ can be made based on the observation that, in regions of low transmit or receive sensitivity, the determination of field amplitudes $|B_1^{(+)}|$ or $|MB_1^{(-)}|$ as well as of phases $\phi_\Sigma$ and $\phi_\Delta$ becomes unreliable. Furthermore, the exemplary quantities $\nabla \ln|B_1^{(+)}|$ and $\nabla \ln|MB_1^{(-)}|$ are ill-defined and error-prone in these regions. Therefore, a simple choice of diagonal noise covariance matrix $$\begin{bmatrix} \Psi_{ll} & 0 \\ 0 & \Psi_{l'l'} \end{bmatrix} \propto \begin{bmatrix} |B_{1,l}^{(+)}| & 0 \\ 0 & |MB_{1,l'}^{(-)}| \end{bmatrix} \quad (30)$$

can selectively remove coils with unreliable amplitude and phase estimates from the reconstruction, improving the result. In order for the resulting inverse problem to remain well posed, however, coils or coil combinations l and l' must be chosen such that sensitivities are not simultaneously low at the same spatial positions in multiple coils. Alternatively, local coil combinations which prevent the occurrence of sensitivity nulls may be used.

Another way of improving the robustness of LMT reconstruction can be to choose RF coils or coil combinations such that the condition number of the encoding matrix A is kept as low as possible so as to yield the highest possible SNR via Eq. (29). Since the exemplary encoding matrix in the exemplary LMT can consist of various directional derivatives, it can be important to ensure that there is suitable field variation along all directions in regions of interest. For example, the use of an encircling loop or strip elements with a large extent along the $B_0$ field direction z can lead to singularity of the encoding matrix for centrally-located voxels, since the z gradients of field amplitudes and phases then tend to vanish for all coil elements. As may be appreciated from Eq. (20), this leaves $\nabla_z\phi_0$ unconstrained, which in turn can remove constraints on $\nabla\phi_0\cdot\nabla\phi_0$, and render the solution for permittivity non-unique (which can correspond to a singular matrix $\tilde{A}$). If the condition number of the exemplary encoding matrix increases beyond a certain limit, errors in A may no longer be neglected as in Eq. (28), and alternative approaches may be taken to estimation of error propagation and to optimized reconstruction.

EPT as a special case of LMT: EPT is based on the fundamental assumption that, for a birdcage coil operated with a traditional quadrature hybrid, the reversal of effective circular polarization between transmission and reception results in very similar transmit and receive field phase distributions: $\phi_{B_1^{(+)}} \approx \phi_{B_1^{(-)}}$. To the extent that this assumption holds true, the phase of the MR signal in Eq. (6) becomes $2\phi_{B_1^{(+)}} + \phi_M$, and correction for or minimization of any background phase $\phi_M$ can result in full knowledge of the transmit field phase $\phi_{B_1^{(+)}}$, perhaps up to an overall constant phase. Thus, it is possible to set $\phi_0 \approx$ constant, yielding $\nabla\phi_0 \approx 0$ and $\nabla^2\phi_0 \approx 0$. In this case, Eq. (15) simplifies to $$\left(\frac{\nabla^2|B_l^{(+)}|}{|B_l^{(+)}|} - \nabla\varphi_{B_1^{(+)}} \cdot \nabla\varphi_{B_1^{(+)}}\right) = -\omega^2\mu\varepsilon \quad (31)$$

-continued $$\left(\frac{2\nabla|B_1^{(+)}|\cdot\nabla\varphi_{B_1^{(+)}}}{|B_1^{(+)}|}+\nabla\varphi_{B_1^{(+)}}\right)=-\omega\mu\sigma$$

These exemplary equations represent one embodiment of the EPT equations, which may be solved using techniques known to those skilled in the art. Thus, EPT represents just one special case of the more general LMT formalism. The central EPT approximation $\phi_{B_1}^{(+)} \approx \phi_{B_1}^{(-)}$ is reliable at low field strength or in selected situations of suitable symmetry in the geometry of the imaged subject and the coil. In removing the EPT phase approximation, the exemplary LMT can eliminate the need for such symmetries and opens up a broader range of allowed coil designs and field strengths, at the cost of increased requirements for data acquisition and reconstruction.

Exemplary Local shimming for simplified solution of the LMT master equations: The generalized multicoil framework of LMT can provide additional flexibility to choose different combinations of coils in different regions to simplify image reconstruction. Indeed, with the measured data in Eq.'s (6)-(10), one can use relative transmit and receive field phases and amplitudes to find local combinations of transmit or receive coils such that $$\nabla|B_{1,composite}^+|\approx 0$$

$$\nabla|MB_{1,composite}^-|\approx 0 \quad (32)$$

over suitably small regions of interest (e.g. the same regions over which local derivatives are computed). This exemplary local magnitude shimming approach can drive the majority of the field variation into the phase, and results in the following simplified LMT equations involving conductivity:

$$\omega\mu\sigma=+\nabla^2\phi_0-\nabla^2\phi_{\Sigma composite}$$

$$\omega\mu\sigma=-\nabla^2\phi_0-\nabla^2\phi_{\Delta composite}+2(\nabla\phi_{\Delta composite}+\nabla\phi_0)\cdot\nabla\ln|M| \quad (33)$$

In the case of piecewise constant magnetization (or other cases in which the term involving |M| in Eq. (33) is small), these equations have a particularly simple solution:

$$\sigma\approx-(\nabla^2\phi_{\Sigma composite}+\nabla^2\phi_{\Delta composite})/2\omega\mu$$

$$\nabla^2\phi_0\approx(\nabla^2\phi_{\Sigma composite}-\nabla^2\phi_{\Delta composite})/2 \quad (34)$$

Unlike for Eq. (34), the phase gradient $\nabla\phi_0$ does not vanish from the equations involving permittivity, and so a simple local shimming approach with one transmit and one receive field combination is insufficient to fix the four unknowns in $\nabla\phi_0$ and $\in$. However, with values of $\sigma$ and $\nabla^2\phi_0$ in hand, it is straightforward to return to the un-shimmed equations (21) or (26) to derive the values of $\nabla\phi_0$, from which $\in$ can then be derived via Eq. (24) or (27) as described earlier for the general LMT procedure. The exemplary local shimming approach can be viewed as a kind of physical back-substitution procedure which, though in principle may be no better conditioned than general LMT, may have certain advantages of stability and simplicity. The local shimming approach also has an alternative interpretation as a way of enforcing ideal EPT-like behavior at each position of interest. Given the definitions $\phi_{\Sigma composite}=\phi_{B_{1,composite}}^{(+)}+\phi_0$ and $\phi_{\Delta composite}=\phi_{B_{1,composite}}^{(-)}-\phi_0$, the first line in Eq. (34) may be rewritten as $$\sigma\approx-\nabla^2(\phi_{B_{1,composite}}^{(+)}+\phi_{B_{1,composite}}^{(-)})/2\omega\mu \quad (35)$$

The phase sum $\phi_{B_{1,composite}}^{(+)}+\phi_{B_{1,composite}}^{(-)}$ is just the phase of the MR signal formed by combining signals from different transmitters according to the local transmit shim, and signals from different receivers according to the local receive shim. The net result can be a single composite signal which, when background phase $\phi_M$ is removed, behaves like an ideal EPT birdcage signal in the sense that the curvature of transmit and receive phases are each directly proportional to the conductivity (e.g., even if these phases themselves are not necessarily equal), and there therefore may be no need to separate them. It may be that only when rapidly varying magnetization interferes with the receive field shim will the locally-adjusted EPT condition fail to hold rigorously.

Choice of exemplary derivative algorithm: Any suitable numerical derivative procedure can be selected to compute the matrix and vector elements in the LMT master equations. The formalism does not assume any particular choice of quadrature for derivative estimation, thus embodiments of the exemplary LMT can be free to use whichever algorithm works most robustly for a case or even a voxel of interest. Exemplary embodiments can use Savitsky-Golay (SG) derivatives, in which the function to be differentiated can be fitted to a low-order polynomial over a small kernel region around each voxel, and analytic derivatives of the best-fit polynomial can be computed.

Exemplary phase unwrapping: Field phases $\phi(x, y, z)$ are typically more slowly varying than complex exponentials $\exp(i\phi(x, y, z))$, and can therefore be better suited to SG derivative estimation. However, exemplary phase wrapping can cause artificially high derivative values in the vicinity of $2\pi$ discontinuities. Exemplary embodiments according to the present disclosure can use a simple unwrapping procedure taking advantage of the fact that only phase derivatives and not the phase values themselves are of interest. The source complex exponentials defining measured phases can be incremented by a fixed phase in multiple steps ranging from 0 to $2\pi$, thereby shifting the location of phase discontinuities, and the phase functions and their derivatives can be recomputed for each increment. The median derivative value can then be selected as the true derivative, since only a small minority of increments may result in a phase discontinuity within the small computation kernel and in a corresponding anomalous derivative value.

Exemplary local coil recombination: The concept of region-by-region shimming introduced in the description of a simplified LMT solution above can also be valuable in improving the accuracy of the exemplary LMT matrix and its inverse. As was mentioned earlier, SG derivative estimates may be particularly error-prone in regions of low transmit or receive sensitivity, and these errors may propagate unfavorably into the exemplary LMT reconstruction. In an attempt to maximize signal and minimize dynamic range, exemplary embodiments can also use all-but-one transmit coil combinations. These combinations, though useful over much of the field of view, typically result in destructive interference in certain regions, often yielding even more rapid field variation and more pathological derivative errors than single-coil transmission. However, the LMT master equations can apply for any combination of coils that satisfies the Maxwell equations, and, the combinations used need not remain constant from region to region. Thus, in order to avoid derivative estimation errors in regions of excessively rapid field variation for any given coil, exemplary embodiments can use a local matched filter field recombination approach in which known phase relations between transmit and receive fields at the center of each SG kernel can be used to ensure constructive interference and to create synthetic coil sets with comparatively slow field variation over the kernel. In particular, for each voxel and its corresponding SG kernel, exemplary embodiments can use the amplitudes $|B_{1,l}^{(+)}|$ and relative phases $\phi_{\Sigma_l}$ to form the following set of composite field combinations $\tilde{B}_{1,l}^{(+)}$:

$$\begin{bmatrix} \tilde{B}_{1,1}^{(+)}(x,y,z) \\ \tilde{B}_{1,2}^{(+)}(x,y,z) \\ \vdots \\ \tilde{B}_{1,L}^{(+)}(x,y,z) \end{bmatrix} = \begin{bmatrix} 0 & |B_{1,2}^{(+)}|\exp(-i\varphi_{\Sigma_2})|_{(x_0,y_0,z_0)} & \cdots & |B_{1,L}^{(+)}|\exp(-i\varphi_{\Sigma_L})|_{(x_0,y_0,z_0)} \\ |B_{1,1}^{(+)}|\exp(-i\varphi_{\Sigma_1})|_{(x_0,y_0,z_0)} & 0 & \cdots & |B_{1,L}^{(+)}|\exp(-i\varphi_{\Sigma_L})|_{(x_0,y_0,z_0)} \\ \vdots & \vdots & \ddots & \vdots \\ |B_{1,1}^{(+)}|\exp(-i\varphi_{\Sigma_1})|_{(x_0,y_0,z_0)} & |B_{1,2}^{(+)}|\exp(-i\varphi_{\Sigma_1})|_{(x_0,y_0,z_0)} & \cdots & 0 \end{bmatrix} \quad (36)$$

$$\square \begin{bmatrix} |B_{1,1}^{(+)}(x,y,z)|\exp(i\varphi_{\Sigma_1}(x,y,z)) \\ |B_{1,2}^{(+)}(x,y,z)|\exp(i\varphi_{\Sigma_2}(x,y,z)) \\ \vdots \\ |B_{1,L}^{(+)}(x,y,z)|\exp(i\varphi_{\Sigma_L}(x,y,z)) \end{bmatrix}$$

Such exemplary approach entails forming a matched filter combination by rephasing each coil by its relative phase at the kernel center $(x_0, y_0, z_0)$, multiplying by its sensitivity at that point, and summing, then subtracting each rephased coil in turn from the matched filter baseline combination to yield a set of complex fields whose amplitude and phase can then be used for LMT. The availability of full field amplitude and relative phase information at every spatial location can facilitate an exemplary local post-acquisition retuning of the all-but-one approach which can avoid destructive interference and corresponding rapid field variation and/or signal nulls which would otherwise be unavoidable with spatially invariant coil combinations. Since a single weighted combination based on the kernel center is used over the entire kernel in this approach, the underlying spatial variation of fields is not modified artificially, and Maxwell's equations continue to apply. A combination similar to Eq. (36) can also be performed for receive fields, using known values of $|MB_{1,l'}^{(-)}|$ and $\phi_{\Delta_{l'}}$.

The exemplary reference coil combination used to define the missing phase $\phi_0$ also need not remain constant from region to region, as long as it does not change within each region. Thus, a local matched filter combination can also be used to minimize destructive interference which might contribute to phase uncertainty:

$$\varphi_{\Sigma_l}(x,y,z) = \angle\left(\sum_{l'}\left(\sum_l S^*_{l,l'}(x_0,y_0,z_0)\right)S_{l,l'}(x,y,z)\right) - \varphi_M \quad (37)$$

$$\varphi_{\Delta_{l'}}(x,y,z) = \angle\left(\sum_l S_{l,l'}(x,y,z)\exp(-i\varphi_{\Sigma_l}(x,y,z))\right) - \varphi_M$$

Exemplary consensus solutions using particular choices of exemplary derivative discretization: An alternative approach to formulation and solution of the exemplary LMT master equations can involve choosing a particular discretization for local derivatives in advance and rewriting the equations in discrete form. For example, assuming a regular grid of voxels defined by coordinates $(x_i, y_j, z_k)$, the terms of the Laplacian operator can be approximated with simple finite differences on that grid:

$$\frac{\partial^2 B_{\alpha,l}}{\partial x^2} \approx \frac{B_{\alpha,l}(x_{i+1}, y_j, z_k) - 2B_{\alpha,l}(x_i, y_j, z_k) + B_{\alpha,l}(x_{i-1}, y_j, z_k)}{\Delta x^2} \quad (38)$$

More advanced quadrature can also be selected for more accurate approximations of the second derivative. The simple choice of quadrature in Eq. (38), inserted into Eq. (4), results in the following expression:

$$\left\{\frac{B_{\alpha,l}(x_{i+1}, y_j, z_k) + B_{\alpha,j}(x_{i-1}, y_j, z_k)}{\Delta x^2} + \frac{B_{\alpha,l}(x_i, y_{j+1}, z_k) + B_{\alpha,l}(x_i, y_{j-1}, z_k)}{\Delta y^2} + \frac{B_{\alpha,l}(x_i, y_j, z_{k+1}) + B_{\alpha,l}(x_i, y_j, z_{k-1})}{\Delta z^2}\right\} - \quad (39)$$

$$\left(\frac{2}{\Delta x^2} + \frac{2}{\Delta y^2} + \frac{2}{\Delta z^2}\right)B_{\alpha,l}(x_i, y_j, z_k) \approx$$

$$-i\omega\mu(\sigma - i\omega\varepsilon)B_{\alpha,l}(x_i, y_j, z_k) \text{ or}$$

$$\left\{\frac{B_{\alpha,l}(x_{i+1}, y_j, z_k) + B_{\alpha,l}(x_{i-1}, y_j, z_k)}{\Delta x^2} + \frac{B_{\alpha,l}(x_i, y_{j+1}, z_k) + B_{\alpha,l}(x_i, y_{j-1}, z_k)}{\Delta y^2} + \frac{B_{\alpha,l}(x_i, y_j, z_{k+1}) + B_{\alpha,l}(x_i, y_j, z_{k-1})}{\Delta z^2}\right\} \approx \quad (40)$$

$$\left\{-i\omega\mu(\sigma - i\omega\varepsilon) + \left(\frac{2}{\Delta x^2} + \frac{2}{\Delta y^2} + \frac{2}{\Delta z^2}\right)\right\}B_{\alpha,l}(x_i, y_j, z_k)$$

Defining $$b_{l1}^{(ijk)} \equiv B_{\alpha,l}(x_{i+1}, y_j, z_k)/B_{\alpha,l}(x_i, y_j, z_k)\Delta x^2$$

$$b_{l2}^{(ijk)} \equiv B_{\alpha,l}(x_{i-1}, y_j, z_k)/B_{\alpha,l}(x_i, y_j, z_k)\Delta x^2$$

$$b_{l3}^{(ijk)} \equiv B_{\alpha,l}(x_i, y_{j+1}, z_k)/B_{\alpha,l}(x_i, y_j, z_k)\Delta x^2$$

$$b_{l4}^{(ijk)} \equiv B_{\alpha,l}(x_i, y_{j-1}, z_k)/B_{\alpha,l}(x_i, y_j, z_k)\Delta x^2$$

$$b_{l5}^{(ijk)} \equiv B_{\alpha,l}(x_i, y_j, z_{k+1})/B_{\alpha,l}(x_i, y_j, z_k)\Delta z^2$$

$$b_{l6}^{(ijk)} \equiv B_{\alpha,l}(x_i, y_j, z_{k-1})/B_{\alpha,l}(x_i, y_j, z_k)\Delta z^2 \quad (41)$$

and $$c \equiv -i\omega\mu(\sigma - i\omega\varepsilon) + \left(\frac{2}{\Delta x^2} + \frac{2}{\Delta y^2} + \frac{2}{\Delta z^2}\right) \quad (42)$$

we have $$b_{I1}^{(ijk)} + b_{I2}^{(ijk)} + b_{I3}^{(ijk)} + b_{I4}^{(ijk)} + b_{I5}^{(ijk)} + b_{I6}^{(ijk)} \approx c \quad (43)$$

If true field components are expressed as products of measurable quantities with unknown quantities as in Eq.'s (11) and (12), then Eq. (43) can be rewritten separating known and unknown quantities:

$$\tilde{b}_{I1}^{(ijk)} p_1^{(ijk)} + \tilde{b}_{I2}^{(ijk)} p_2^{(ijk)} + \tilde{b}_{I3}^{(ijk)} p_3^{(ijk)} + \tilde{b}_{I4}^{(ijk)} p_4^{(ijk)} + \tilde{b}_{I5}^{(ijk)} p_5^{(ijk)} + \tilde{b}_{I6}^{(ijk)} p_6^{(ijk)} \approx c \quad (44)$$

where, for the case of Eq. (11), $$\tilde{b}_{I1}^{(ijk)} \equiv \quad (45)$$

$$\frac{B_{1+,l}(x_{i+1}, y_j, z_k)}{B_{1+,l}(x_i, y_j, z_k)\Delta x^2} e^{i\left(\varphi_{B_{1-},l_0}(x_{i+1}, y_j, z_k) - \varphi_{B_{1-},l_0}(x_i, y_j, z_k)\right)}$$

$$p_1^{(ijk)} \equiv e^{-i\left(\varphi_{B_{1-},l_0}(x_{i+1}, y_j, z_k) - \varphi_{B_{1-},l_0}(x_i, y_j, z_k)\right)}$$

and, for the case of Eq. (12), $$\tilde{b}_{I1}^{(ijk)} \equiv \frac{|M(x_{i+1}, y_j, z_k)|B_{1+,l'}(x_{i+1}, y_j, z_k)}{|M(x_i, y_j, z_k)|B_{1+,l'}(x_i, y_j, z_k)\Delta x^2} \quad (46)$$

$$e^{-i\left(\varphi_{B_{1-},l_0}(x_{i+1}, y_j, z_k) - \varphi_{B_{1-},l_0}(x_i, y_j, z_k)\right)}$$

$$p_1^{(ijk)} \equiv \frac{|M(x_i, y_j, z_k)|}{|M(x_{i+1}, y_j, z_k)|} e^{+i\left(\varphi_{B_{1-},l_0}(x_{i+1}, y_j, z_k) - \varphi_{B_{1-},l_0}(x_i, y_j, z_k)\right)}$$

Similar definitions apply for each of the remaining 5 sets of terms in each case.

For the case of multicoil transmission (with a total of L transmit coils) for a single receive channel, a system of equations may be written:

$$\tilde{b}_{11}^{(ijk)} p_1^{(ijk)} + \tilde{b}_{12}^{(ijk)} p_2^{(ijk)} + \tilde{b}_{13}^{(ijk)} p_3^{(ijk)} + \tilde{b}_{14}^{(ijk)} p_4^{(ijk)} + \tilde{b}_{15}^{(ijk)} p_5^{(ijk)} + \tilde{b}_{16}^{(ijk)} p_6^{(ijk)} \approx c$$

$$\tilde{b}_{21}^{(ijk)} p_1^{(ijk)} + \tilde{b}_{22}^{(ijk)} p_2^{(ijk)} + \tilde{b}_{23}^{(ijk)} p_3^{(ijk)} + \tilde{b}_{24}^{(ijk)} p_4^{(ijk)} + \tilde{b}_{25}^{(ijk)} p_5^{(ijk)} + \tilde{b}_{26}^{(ijk)} p_6^{(ijk)} \approx c$$

...

$$\tilde{b}_{L1}^{(ijk)} p_1^{(ijk)} + \tilde{b}_{L2}^{(ijk)} p_2^{(ijk)} + \tilde{b}_{L3}^{(ijk)} p_3^{(ijk)} + \tilde{b}_{L4}^{(ijk)} p_4^{(ijk)} + \tilde{b}_{L5}^{(ijk)} p_5^{(ijk)} + \tilde{b}_{L6}^{(ijk)} p_6^{(ijk)} \approx c \quad (47)$$

or, in matrix form, $$\underline{\underline{b}^{(ijk)}}_{known} \underline{p^{(ijk)}}_{unknown} \approx \underline{c^{(ijk)}}_{unknown} I_L \quad (48)$$

with $I_L$ representing an L-dimensional vector with elements all equal to 1. Equations similar to Eq. (48) may be formulated for both transmit and receive fields, e.g.

$$b_+ p_+ = c I_L$$

$$b_- p_- = c I_L = b_- \text{diag}(|p_-|) p_+^* \quad (49)$$

The complementary relationship between transmit and receive fields can be reflected by the complex conjugation in Eq. (49). In one embodiment, these discretized master equations may be solved by enforcement of self-consistency among multiple complementary estimations of electrical property distributions based on distinct measurements. For example, a nonlinear optimization problem may be solved by searching for values of the missing quantities that minimize cost or energy functions like the following:

$$\min_{\{p_+, |p_-|\}} L = \lambda_1 \|b_+ p_+ - b_- \text{diag}(|p_-|) p_+^*\|_{2n} + \quad (50)$$

$$\lambda_2 \frac{\text{var}(b_+ p_+)}{|\text{mean}(b_+ p_+)|^{2n}} + \lambda_3 \frac{\text{var}(b_- \text{diag}(|p_-|) p_+^*)}{|\text{mean}(b_- \text{diag}(|p_-|) p_+^*)|^{2n}}$$

The balanced cost function in Eq. (50) can simultaneously penalize variances among transmit coil property estimates (term 2), variances among receive coil estimates (term 3), and differences between transmit and receive estimates (term 1). The exemplary relative weight of each term may be controlled by appropriate weighting parameters $\lambda_1$, $\lambda_2$, $\lambda_3$. Once values of the unknowns which minimize the cost function have been found, electrical properties can be derived from consensus values of the quantity c in Eq. (49).

Figure 2:
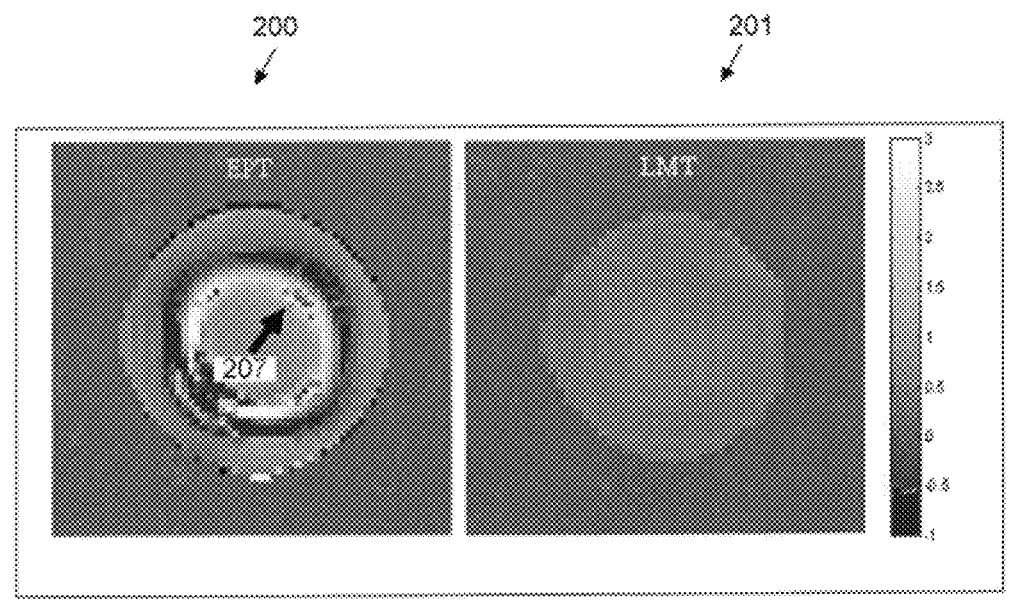
FIG. 2 shows an exemplary simulation comparing conductivity maps, according to another exemplary embodiment of the present disclosure.

Experimental confirmation: Certain exemplary embodiments described herein have also been implemented, tested, and confirmed both in numerical simulations and experimental measurements. FIG. 1 shows numerical simulations of conductivity maps comparing EPT 100 (e.g., simulated birdcage coil) with LMT 101 (e.g., birdcage rungs used as 16 individual elements) in a simplified cylindrical body model with heart, lung, spinal cord, kidney, and muscle compartments assigned literature values of electrical properties at 300 MHz (corresponding to the proton Larmor frequency for 7 Tesla field strength). Elements 105 and 107 show artifacts due to derivative errors 105 and EPT phase assumption errors 107, which are removed by LMT. FIG. 2 shows results of experiments at 7 Tesla field strength comparing conductivity maps for EPT 200 (e.g., birdcage) with LMT 201 (e.g., encircling loop array with 8 transmit and 16 receive elements) in a single-compartment cylindrical phantom. Ring artifacts 207 in EPT due to a null in birdcage sensitivity and corresponding derivative errors are removed by LMT, which yields correct electrical property values (validated by dielectric probe) as well as a correct spatial distribution.

The simulations shown in FIG. 1 use Finite Difference Time Domain software executed by a computer processor to compute magnetic fields resulting from a time-harmonic stimulus in the selected coils. Measurable quantities were formed from computed fields, and these quantities were used for electrical property map reconstruction without reference to true fields or electrical properties.

For the experiments shown in FIG. 2, a multiecho modified Actual Flip Angle imaging (AFI) sequence was used for volumetric multi-coil $B_1$ mapping as well as $B_0$ mapping to remove background non-electrodynamic phase $\phi_M$. A low-flip-angle gradient echo (GRE) sequence was used to generate MR signals for sum phase $\phi_\Sigma$, difference phase $\phi_\Delta$, and $|MB_1^{(-)}|$ determination. Particular optimized methods for phase and amplitude determination were used, reducing the number of time-consuming transmit sensitivity mapping acquisitions required. However, other methods known to those skilled in the art may also be used in particular exemplary embodiments according to the present disclosure.

For both simulations and experiments shown in FIGS. 1 and 2, the exemplary linear two-step LMT procedure, assuming constant local magnetization, was used. SG derivatives were used, with a polynomial order of 2. For noise-free finite difference time domain simulations in which spatial derivatives are defined by nearest neighbor relations on a grid (FIG. 1), a kernel size of 3 in all three dimensions was used, with independent separable polynomial fits in each direction, since this best matches the ground truth of the simulated fields. For experimental data (see FIG. 2) a kernel size of 7 in all three dimensions centered around each voxel was used, and a nonseparable three-dimensional polynomial fit $f(x,y,z) \approx p_1 + p_2 x + p_3 y + p_4 z + p_5 x^2 + p_6 y^2 + p_7 z^2 + p_8 xy + p_9 xz + p_{10} yz$ was found to have good performance. In general, noise averaging increases but systematic error related to the finite polynomial fit order increases as kernel size increases, and moderate kernel sizes can provide a reasonable balance. The local matched filter coil recombination approach was used, as it was found to perform significantly more robustly than coil-by-coil LMT, even when using a field-amplitude-weighted least squares solution with $\Psi$ taking the form of Eq. (30).

Reconstruction times for custom-designed Matlab code were approximately 0.1 sec per voxel, for our particular choice of numerical derivative algorithm. Substantial increases in reconstruction speed may be expected both from use of compiled code and from trivial voxel-wise parallelization, e.g., using the parallel Matlab toolbox or other multicore/GPU implementations. Nonlinear reconstruction including variable local magnetization density was found to increase reconstruction times by a factor of 2-3. The choice of whether to include magnetization gradients as unknowns can be dictated by prior knowledge about the imaged object, or by a desire for full generality. (Since regions of constant electrical properties may often represent consistent tissue types, rapid changes in magnetization may not be expected to be common over these regions, enabling simplified reconstructions which may always be tested subsequently by expanding the unknowns to include magnetization.) The ability to generate pure maps of magnetization density, unperturbed by field-related quantities, can indicate another potentially useful capability of LMT, with applications, e.g., in quantitative imaging.

Figure 3:
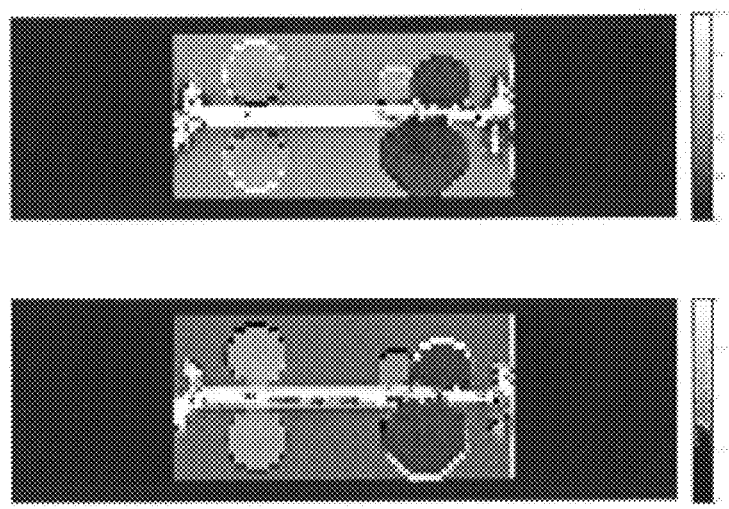
FIG. 3 shows an alternative exemplary reconstruction of electrical property distributions, according to another exemplary embodiment of the present disclosure.

FIG. 3 illustrates an alternative reconstruction of electrical property distributions (including both permittivity and conductivity) obtained using an exemplary pre-discretized consensus reconstruction procedure on simulated data with noise added (average SNR of 200 for MR signal, 20 for $B_{1+}$ maps) in the same simple body model used for FIG. 1.

Figure 4:
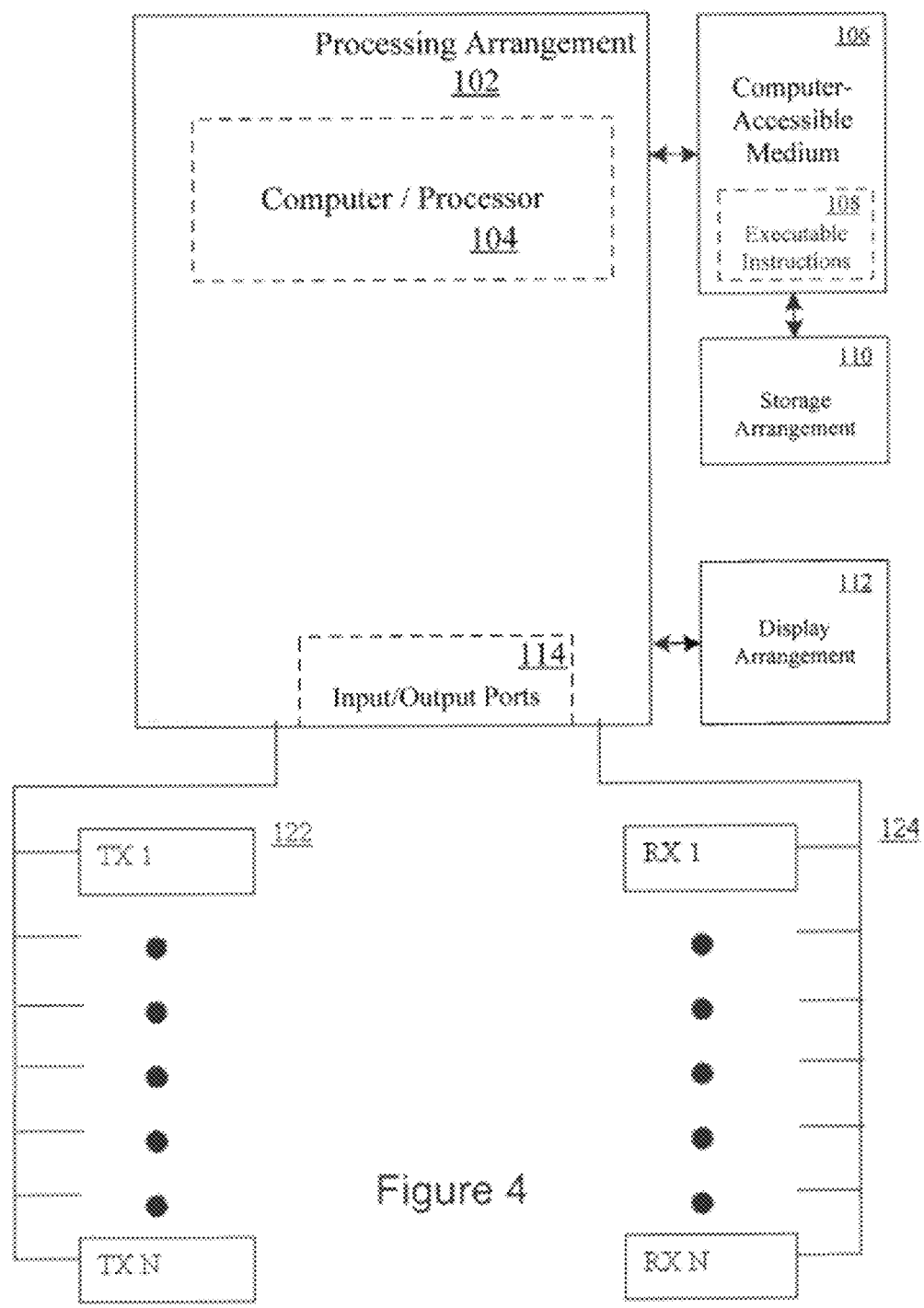
FIG. 4 is a block diagram of an exemplary embodiment of a system according to the present disclosure.

FIG. 4 shows an exemplary block diagram of an exemplary embodiment of a system according to the present disclosure. For example, exemplary procedures in accordance with the present disclosure described herein can be performed by transmitters 122 (TX 1 through TX N), receivers 124 (RX 1 through RX N), and a processing arrangement and/or a computing arrangement 102. Such processing/computing arrangement 102 can be, e.g., entirely or a part of, or include, but not limited to, a computer/processor 104 that can include, e.g., one or more microprocessors, and use instructions stored on a computer-accessible medium (e.g., RAM, ROM, hard drive, or other storage device).

As shown in FIG. 4, e.g., a computer-accessible medium 106 (e.g., as described herein above, a storage device such as a hard disk, floppy disk, memory stick, CD-ROM, RAM, ROM, etc., or a collection thereof) can be provided (e.g., in communication with the processing arrangement 102). The computer-accessible medium 106 can contain executable instructions 108 thereon. In addition or alternatively, a storage arrangement 110 can be provided separately from the computer-accessible medium 106, which can provide the instructions to the processing arrangement 102 so as to configure the processing arrangement to execute certain exemplary procedures, processes and methods, as described herein above, for example.

Further, the exemplary processing arrangement 102 can be provided with or include an input/output arrangement 114, which can include, e.g., a wired network, a wireless network, the internet, an intranet, a data collection probe, a sensor, etc. As shown in FIG. 4, the exemplary processing arrangement 102 can be in communication with an exemplary display arrangement 112, which, according to certain exemplary embodiments of the present disclosure, can be a touch-screen configured for inputting information to the processing arrangement in addition to outputting information from the processing arrangement, for example. Further, the exemplary display 112 and/or a storage arrangement 110 can be used to display and/or store data in a user-accessible format and/or user-readable format.

Figure 5:
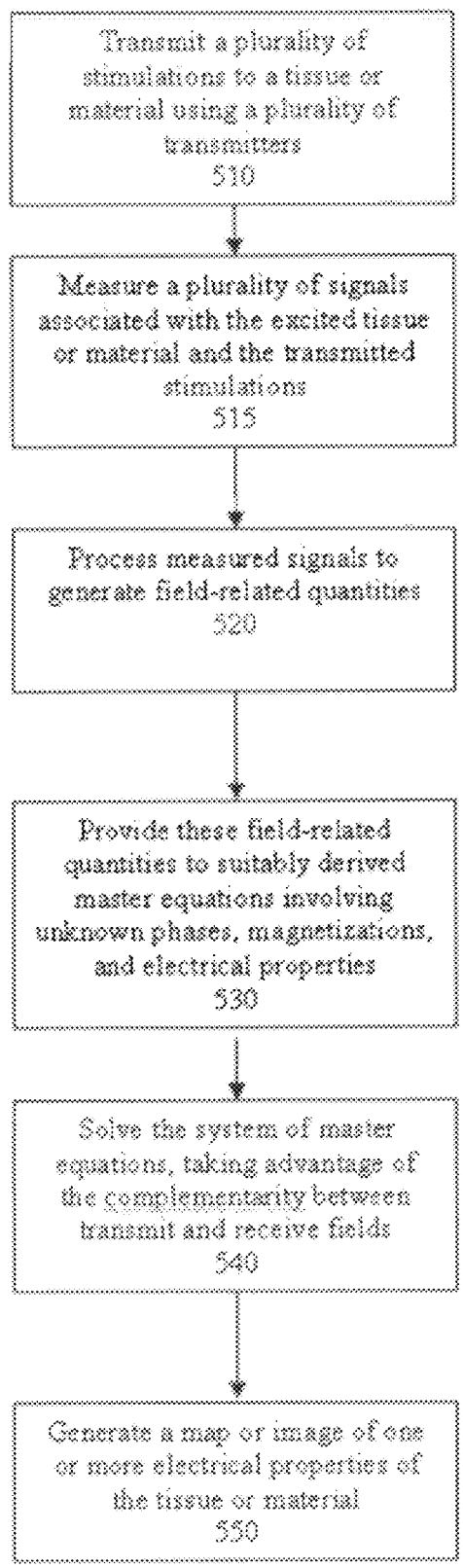
FIG. 5 is a flow diagram of an exemplary embodiment of a method according to the present disclosure.

One exemplary embodiment of the LMT approach can include the following steps, as shown in FIG. 5. First at procedure 510, the exemplary method can implement a magnetic resonance imaging seamier equipped with at least one transmit channel and at least one receive channel to measure several variables. For example, at procedure 515, the exemplary method can measure a magnetic resonance signal resulting from excitation of the imaged body via each of a plurality of transmit coils and reception in each of a plurality of detector coils. Each transmit and receive coil may be connected to a distinct transmit or receive channel in the MR scanner, or else distinct coils may be interfaced sequentially to a smaller number of channels, or else a smaller number of coils may be moved sequentially into distinct positions to accomplish equivalent measurements. The exemplary method can determine a transmit field amplitude map in the imaged body associated with each of the plurality of transmit coils. Additionally, the exemplary method can determine a phase map of the magnetization distribution in the imaged body.

Next, at procedure 520, the exemplary method can generate, from such measurements, a set of quantities representing the true laboratory-frame complex RF transmit and receive field distributions for each transmit and receive coil, e.g., each multiplied by factors involving unknown phases and magnetizations common to all coils. Next, at procedure 530, the exemplary method can provide these quantities, and/or any appropriate derivatives thereof, to suitably derived LMT master equations relating measured field-related quantities to functions of unknown phases, magnetizations, and electrical conductivity and permittivity values. At procedure 540, the exemplary method can solve a system of exemplary equations using any of the techniques outlined in this disclosure or other appropriate techniques to determine values of electrical properties and other unknowns. Finally, at 550, the exemplary embodiment can generate maps or images of the resulting electrical properties throughout the imaged body.

Figure 6:
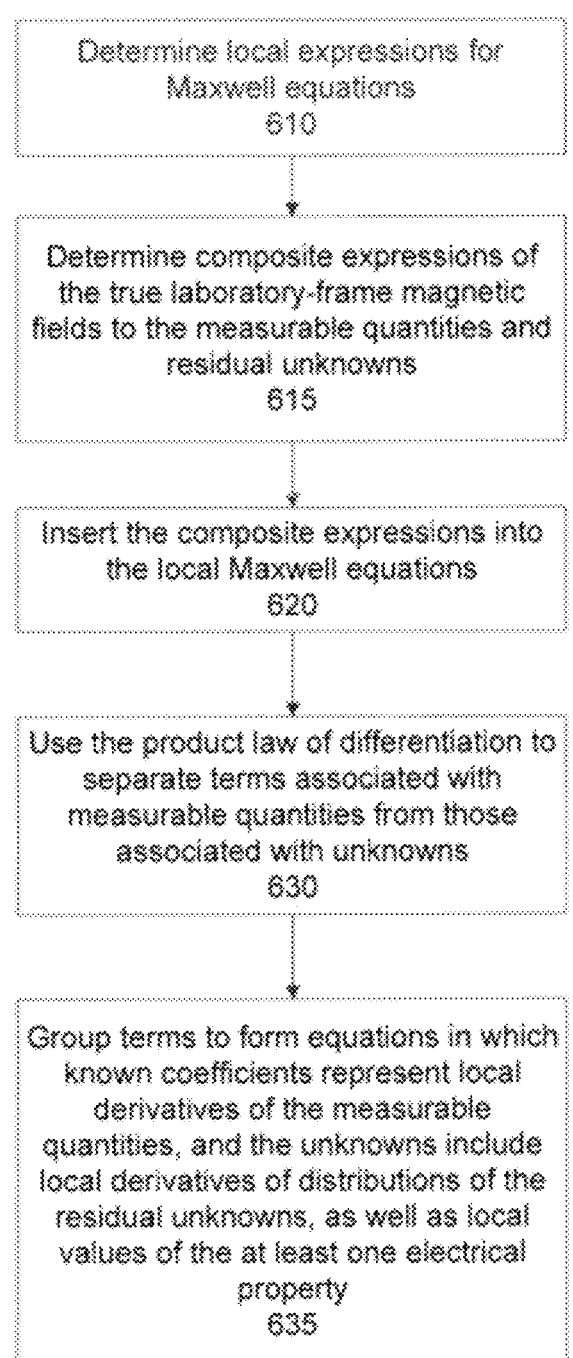
FIG. 6 is a flow diagram of an exemplary embodiment of a method according to the present disclosure.

FIG. 6 illustrates an exemplary embodiment for deriving the system of equations, e.g., as discussed in FIG. 5, element 530. At 610, the exemplary procedure can determine local expressions for Maxwell equations relating field curvature to electrical properties of interest. Next, at 615, the exemplary procedure can determine composite expressions by expressing the true laboratory-frame magnetic fields as combinations of measurable quantities and residual unknowns. The measurable quantities can include those quantities that can be directly measured, as well as quantities derived from the directly measurable quantities or a combination thereof. Next, at 620, the exemplary procedure can insert these composite expressions into the local Maxwell equations. At 630, the exemplary procedure can use the product law of differentiation to separate terms associated with measurable quantities from those associated with the residual unknowns. Finally, at 635, the exemplary procedure can group the terms to form equations in which known coefficients represent local derivatives of the measurable quantities, and the unknowns include local derivatives of distributions of the residual unknowns, as well as local values of the at least one electrical property.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. In addition, all publications and references referred to above can be incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly being incorporated herein in its entirety. All publications referenced above can be incorporated herein by reference in their entireties.

What is claimed is:

1. A method for determining at least one electrical property of at least one target, comprising:
   applying a plurality of stimulation radiations to the at least one target;
   receiving at least one signal from the at least one target in response to the applied radiations;
   determining electromagnetic-field-related quantities associated with the at least one signal provided from the at least one target;
   providing the electromagnetic-field-related quantities to procedures to relate the electromagnetic-field-related quantities to a plurality of unknown electrical property values and residual field-related unknown values of the at least one target; and
   using a computer hardware arrangement, determining the at least one electrical property of the at least one target based on the determination of the procedures.

2. The method of claim 1, wherein the at least one target includes at least one of a tissue or a material.

3. The method of claim 1, wherein the at least one electrical property includes at least one of a conductivity, a permittivity, or a permeability of the at least one target.

4. The method of claim 3, wherein at least one of the conductivity, permittivity, or the permeability is at least one of a scalar or a tensor.

5. The method of claim 1, further comprising:
   mapping the at least one electrical property of the at least one target.

6. The method of claim 1, wherein the stimulations include at least one of an injection of a current or generation of an electromagnetic field.

7. The method of claim 1, wherein the at least one signal includes information representative of at least one of a current or an electromagnetic field.

8. The method of claim 1, wherein the stimulations are created by a plurality of radiofrequency transmitter coils.

9. The method of claim 1, wherein the at least one signal is detected in at least one radiofrequency receiver coil.

10. The method of claim 1, wherein the at least one signal is a magnetic resonance signal.

11. The method of claim 1, wherein the residual field-related unknown values include at least one of an electromagnetic field phase or a magnetization value.

12. The method of claim 1, wherein electromagnetic-field-related quantities include a transmit and/or a receive sensitivity distribution.

13. The method of claim 1, wherein complementary information from transmit and receive sensitivity distributions is used to resolve ambiguities in electrical property values and residual field-related unknown values.

14. The method of claim 1, wherein the procedures include:
   a) determining local expressions for Maxwell equations relating field curvature to electrical properties of interest, including the at least one electrical property of the at least one target;
   b) determining composite expressions by expressing the true laboratory-frame magnetic fields as combinations of measurable quantities and residual unknowns, wherein the measurable quantities include at least one of: directly measurable quantities or quantities derived from the directly measurable quantities;
   c) inserting these composite expressions into the local Maxwell equations, and separating terms associated with measurable quantities from those associated with the residual unknowns and local values of the at least one electrical property; and
   d) grouping the terms to form equations in which known coefficients represent local derivatives of the measurable quantities, and the unknowns include local derivatives of distributions of the residual unknowns, as well as local values of the at least one electrical property.

15. The method of claim 14, wherein separating terms comprises using a product law of differentiation.

16. The method of claim 1, wherein determining the at least one electrical property of the at least one target comprises solving for electrical conductivity and permittivity separately in a plurality of steps.

17. The method of claim 1, wherein determining the at least one electrical property of the at least one target comprises finding and applying one or more linear matrix inverses.

18. The method of claim 1, wherein determining the at least one electrical property of the at least one target comprises applying a nonlinear optimization procedure.

19. The method of claim 1, wherein determining the at least one electrical property of the at least one target includes use of a noise and/or error covariance matrix to control a noise/error propagation.

20. The method of claim 19, wherein the noise/error covariance matrix includes diagonal terms associated with an amplitude of field-related quantities.

21. The method of claim 1, wherein the plurality of stimulations and the at least one signal are selected so as to maintain an acceptable conditioning of a system of equations.

22. The method of claim 21, wherein the selection of stimulations and the at least one signal is aimed at ensuring sufficient transmit and/or receive field variation in all directions for robust solution of the procedures.

23. The method of claim 1, wherein determining the at least one electrical property of the at least one target includes use of Tikhonov regularization.

24. The method of claim 1, wherein a transmit-receive array containing at least three elements is used.

25. The method of claim 1, wherein more than three coil pairs are used to improve conditioning.

26. The method of claim 1, wherein the procedures include local combinations of electromagnetic-field-related quantities which reduce the contributions of some residual field-related unknown values as compared with using uncombined quantities.

27. The method of claim 1 wherein determining the at least one electrical property of the at least one target includes use of at least one Savitsky Golay derivative.

28. The method of claim 1, wherein the procedures include local combinations of electromagnetic-field-related quantities which improve the robustness of solution as compared with using uncombined quantities.

29. The method of claim 28, wherein the combinations are derived from a matched filter or rephased combination.

30. The method of claim 28, wherein the combinations are selected to generate slow local variation in the electromagnetic-field-related quantities.

31. The method of claim 28, wherein the local combinations are performed on transmit-field-related quantities.

32. The method of claim 28, wherein the local combinations are performed on receive-field-related quantities.

33. The method of claim 28, wherein the local combinations are selected to produce a tailored phase reference combination at each point of interest.

34. The method of claim 1, wherein determining the at least one electrical property of the at least one target includes:
deriving a plurality of estimations of at least one unknown value for the at least one target based on the measured characteristics;
determining a consensus of the estimations; and
determining the at least one property of the at least one target using the consensus.

35. The method of claim 1, further comprising:
constructing at least one of transmit sensitivity distributions, receive sensitivity distributions, or at least one combination thereof, each having at least one unknown value for the at least one tissue;
determining a consensus of the at least one transmit sensitivity distributions, receive sensitivity distributions, or combinations thereof; and
determining the at least one property of the at least one tissue based on the consensus.

36. A non-transitory computer readable medium including instructions thereon that are accessible by a hardware processing arrangement, wherein, when the processing arrangement executes the instructions, the processing arrangement is configured to:
apply a plurality of stimulation radiations to the at least one target;
receive at least one signal from the at least one target in response to the applied radiations:
determine electromagnetic-field-related quantities associated with the at least one signal provided from the at least one target;
provide the electromagnetic-field-related quantities to procedures to relate the electromagnetic-field-related quantities to a plurality of unknown electrical property values and residual field-related unknown values of the at least one target; and
determine the at least one electrical property of the at least one target based on the determination of the procedures.

37. The medium of claim 36, wherein the residual field-related unknown values include at least one of an electromagnetic field phase or a magnetization value.

38. The medium of claim 36, wherein electromagnetic-field-related quantities include a transmit and/or a receive sensitivity distribution.

39. The medium of claim 36, wherein complementary information from transmit and receive sensitivity distributions is used to resolve ambiguities in electrical property values and residual field-related unknown values.

40. The medium of claim 36, wherein the procedures include:
a) determining local expressions for Maxwell equations relating field curvature to electrical properties of interest, including the at least one electrical property of the at least one target;
b) determining composite expressions by expressing the true laboratory-frame magnetic fields as combinations of measurable quantities and residual unknowns, wherein the measurable quantities include at least one of: directly measurable quantities or quantities derived from the directly measurable quantities;
c) inserting these composite expressions into the local Maxwell equations, and separating terms associated with measurable quantities from those associated with the residual unknowns and local values of the at least one electrical property; and
d) grouping the terms to form equations in which known coefficients represent local derivatives of the measurable quantities, and the unknowns include local derivatives of distributions of the residual unknowns, as well as local values of the at least one electrical property.

41. The medium of claim 40, wherein separating terms comprises using a product law of differentiation.

42. The medium of claim 36, wherein determining the at least one electrical property of the at least one target comprises solving for electrical conductivity and permittivity separately in two steps.

43. The medium of claim 36, wherein determining the at least one electrical property of the at least one target comprises finding and applying one or more linear matrix inverses.

44. The medium of claim 36, wherein determining the at least one electrical property of the at least one target comprises applying a nonlinear optimization procedure.

45. The medium of claim 36, wherein determining the at least one electrical property of the at least one target includes use of a noise and/or error covariance matrix to control noise/error propagation.

46. The medium of claim 36, wherein determining the at least one electrical property of the at least one target includes use of Tikhonov regularization.

47. The medium of claim 36, wherein the procedures include local combinations of electromagnetic-field-related quantities which reduce the contributions of some residual unknowns as compared with using uncombined quantities.

48. The medium of claim 36 wherein determining the at least one electrical property of the at least one target includes use of at least one Savitsky Golay derivative.

49. The medium of claim 36, wherein the procedures include local combinations of electromagnetic-field-related quantities which improve a robustness of solution as compared with using uncombined quantities.

50. The medium of claim 36, wherein determining the at least one electrical property of the at least one target includes:
- deriving a plurality of estimations of at least one unknown value for the at least one target based on the measured characteristics;
- determining a consensus of the estimations; and
- determining the at least one property of the at least one target using the consensus.

51. An apparatus for determining at least one property of at least one target, the apparatus comprising:
- a plurality of transmitters which is configured to apply a plurality of stimulations to the at least one target;
- a plurality of receivers which is configured to receive at least one signal from the at least one target in response to the applied stimulations; and
- a non-transitory computer readable medium including instructions thereon that are accessible by a hardware processing arrangement, wherein, when the processing arrangement executes the instructions, the processing arrangement is configured to:
- determine electromagnetic-field-related quantities associated with the at least one signal provided from the at least one target;
- provide the electromagnetic-field-related quantities to procedures to relate the electromagnetic-field-related quantities to a plurality of unknown electrical property values and residual field-related unknown values of the at least one target; and
- determine the at least one electrical property of the at least one target based on the determination of the procedures.

52. The apparatus of claim 51, wherein the stimulations include at least one of an injection of a current or generation of an electromagnetic field.

53. The apparatus of claim 51, wherein the at least one signal includes information representative of at least one of a current or an electromagnetic field.

54. The apparatus of claim 51, wherein the stimulations are created by a plurality of radiofrequency transmitter coils, or by one or more transmitter coils moved sequentially to a plurality of locations.

55. The apparatus of claim 51, wherein the at least one signal is detected in at least one radiofrequency receiver coil, or by one or more receiver coils moved sequentially to a plurality of locations.

56. The apparatus of claim 51, wherein the at least one signal is a magnetic resonance signal.

57. The apparatus of claim 51, wherein the residual field-related unknown values include at least one of an electromagnetic field phase or a magnetization value.

58. The apparatus of claim 51, wherein electromagnetic-field-related quantities include a transmit and/or a receive sensitivity distribution.

59. The apparatus of claim 51, wherein complementary information from transmit and receive sensitivity distributions is used to resolve ambiguities in electrical property values and residual field-related unknown values.

60. The apparatus of claim 51, wherein the plurality of stimulations and the at least one signal are selected so as to maintain good conditioning of the procedures.

61. The apparatus of claim 60, wherein the selection of stimulations and the at least one signal is aimed at ensuring sufficient transmit and/or receive field variation in all directions for robust solution of the procedures.

62. The apparatus of claim 51, further comprising:
- a transmit-receive array containing at least three elements.

63. The apparatus of claim 51, further comprising:
- more than three coil pairs used to improve conditioning.

64. A method for determining a magnetization distribution of at least one target, the method comprising:
- applying a plurality of stimulation radiations to the at least one target;
- receiving at least one signal from the at least one target in response to the applied radiations;
- determining electromagnetic-field-related quantities associated with at least one signal provided from the at least one target;
- providing the electromagnetic-field-related quantities to procedures to relate the electromagnetic-field-related quantities to a plurality of unknown magnetization values and residual field-related unknown values of the at least one target; and
- using a computer hardware arrangement, determining at least one magnetization distribution of the at least one target based on the determination of the procedures.

65. A method for determining a field-related phase distribution of at least one target, the method comprising:
- applying a plurality of stimulation radiations to the at least one target;
- receiving at least one signal from the at least one target in response to the applied radiations;
- determining electromagnetic-field-related quantities associated with at least one signal provided from the at least one target;
- providing the electromagnetic-field-related quantities to procedures to relate the electromagnetic-field-related quantities to a plurality of unknown field-related phase values and residual field-related unknown values of the at least one target; and
- using a computer hardware arrangement, determining at least one field-related phase distribution of the at least one target based on the determination of the procedures.

* * * * *